United States Patent
Petrzelka et al.

(10) Patent No.: US 11,033,306 B2
(45) Date of Patent: Jun. 15, 2021

(54) ARTICULATING TOOL AND METHODS OF USING

(71) Applicant: Charles River Engineering Solutions and Technologies, LLC, Chapel Hill, NC (US)

(72) Inventors: Joseph E. Petrzelka, Marine del Rey, CA (US); Manas C. Menon, Boston, MA (US); Suresh K. Agarwal, Chapel Hill, NC (US); Dimitris Chatzigeorgiou, Somerville, MA (US); Michelle E. Lustrino, Cambridge, MA (US); Clara J. Stefanov-Wagner, Cambridge, MA (US)

(73) Assignee: Charles River Engineering Solutions and Technologies, LLC, Chapel Hill, NC (US)

( * ) Notice: Subject to any disclaimer, the term of this patent is extended or adjusted under 35 U.S.C. 154(b) by 257 days.

(21) Appl. No.: 15/935,641

(22) Filed: Mar. 26, 2018

(65) Prior Publication Data
US 2018/0325567 A1    Nov. 15, 2018

Related U.S. Application Data

(63) Continuation of application No. 14/065,259, filed on Oct. 28, 2013, now Pat. No. 9,924,986, which is a
(Continued)

(51) Int. Cl.
*A61B 17/16* (2006.01)
*A61B 17/80* (2006.01)
(Continued)

(52) U.S. Cl.
CPC ........ *A61B 17/808* (2013.01); *A61B 17/1631* (2013.01); *A61B 17/8875* (2013.01);
(Continued)

(58) Field of Classification Search
CPC ............ A61B 17/1615; A61B 17/1617; A61B 17/162; A61B 17/1631; A61B 17/1662;
(Continued)

(56) References Cited

U.S. PATENT DOCUMENTS

| 20,503 A | 6/1858 | Morse |
| 869,697 A | 10/1907 | Eilhauer et al. |

(Continued)

FOREIGN PATENT DOCUMENTS

| AU | 8975091 A | 2/1992 |
| CA | 2452127 A1 | 12/1993 |

(Continued)

OTHER PUBLICATIONS

Cacchione et al, "Painful Nonunion of Multiple Rib Fractures Managed by Operative Stabilization", The Journal of Trauma, Injury, Infection and Critical Care, vol. 48, No. 2, pp. 319-321, 2000.

(Continued)

*Primary Examiner* — Kevin T Truong
*Assistant Examiner* — Tracy L Kamikawa
(74) *Attorney, Agent, or Firm* — Kolisch Hartwell, P.C.

(57) ABSTRACT

Disclosed are embodiments of an articulating tool having a head that articulates and is capable of maintaining an angle for drilling or placing a fastener into a bone. The articulating tool includes a housing, an articulating head, a rotatable drive shaft, and a driver tip connected to the distal shaft portion. The articulating tool may be constructed and arranged to move between a first position and a second position, wherein in the first position and the second position the articulating head and the rotatable drive shaft are at different angles with respect to the longitudinal axis of the housing.

11 Claims, 7 Drawing Sheets

Related U.S. Application Data continuation of application No. 12/886,474, filed on Sep. 20, 2010, now Pat. No. 8,568,417.

(60) Provisional application No. 61/288,198, filed on Dec. 18, 2009.

(51) Int. Cl.
 *A61B 17/88* (2006.01)
 *A61B 17/00* (2006.01)

(52) U.S. Cl.
 CPC ............. A61B 2017/003 (2013.01); *A61B 2017/00318* (2013.01)

(58) Field of Classification Search
 CPC ............ A61B 17/1691; A61B 17/1693; A61B 17/8076; A61B 17/808; A61B 17/823; A61B 17/8875
 See application file for complete search history.

(56) References Cited

U.S. PATENT DOCUMENTS

| | | |
|---|---|---|
| 1,105,105 A | 7/1914 | Sherman |
| 1,156,440 A | 10/1915 | Smith |
| 1,345,425 A | 7/1920 | Wells |
| 1,789,060 A | 1/1931 | Weisenbach |
| 1,889,239 A | 11/1932 | Crowley |
| 1,950,799 A | 3/1934 | Jones |
| 2,042,376 A | 5/1936 | Balga |
| 2,406,832 A | 9/1946 | Hardinge |
| 2,443,363 A | 6/1948 | Townsend et al. |
| 2,489,870 A | 11/1949 | Dzus |
| 2,494,229 A | 1/1950 | Collison |
| 2,496,126 A | 1/1950 | Haboush |
| 2,500,370 A | 3/1950 | McKibbin |
| 2,500,993 A | 3/1950 | Mason |
| 2,526,959 A | 10/1950 | Lorenzo |
| 2,579,968 A | 12/1951 | Rush |
| 2,580,821 A | 1/1952 | Nicola |
| 2,583,896 A | 1/1952 | Siebrandt |
| 2,737,835 A | 3/1956 | Herz |
| 3,025,853 A | 3/1962 | Mason |
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,357,432 A | 12/1967 | Sparks |
| 3,386,437 A | 6/1968 | Treace |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,696,694 A | 10/1972 | Boro |
| 3,716,050 A | 2/1973 | Johnston |
| 3,726,279 A | 4/1973 | Barefoot et al. |
| 3,741,205 A | 6/1973 | Markolf et al. |
| 3,759,257 A | 9/1973 | Fischer et al. |
| 3,774,244 A | 11/1973 | Walker |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,000,525 A | 1/1977 | Klawitter et al. |
| 4,011,863 A | 3/1977 | Zickel |
| 4,055,172 A | 10/1977 | Ender et al. |
| 4,091,806 A | 5/1978 | Aginsky |
| 4,119,092 A | 10/1978 | Gil |
| 4,135,507 A | 1/1979 | Harris |
| 4,169,470 A | 10/1979 | Ender et al. |
| 4,187,840 A | 2/1980 | Watanabe |
| 4,187,841 A | 2/1980 | Knutson |
| 4,201,215 A | 5/1980 | Crossett et al. |
| 4,263,904 A | 4/1981 | Judet |
| 4,327,715 A | 5/1982 | Corvisier |
| 4,364,382 A | 12/1982 | Mennen |
| 4,378,607 A | 4/1983 | Wadsworth |
| 4,388,921 A | 6/1983 | Sutter et al. |
| 4,408,601 A | 10/1983 | Wenk |
| 4,444,181 A | 4/1984 | Wevers et al. |
| RE31,628 E | 7/1984 | Allgower et al. |
| 4,457,307 A | 7/1984 | Stillwell |
| 4,473,069 A | 9/1984 | Kolmert |
| 4,483,335 A | 11/1984 | Tornier |
| 4,484,570 A | 11/1984 | Sutter et al. |
| 4,493,317 A | 1/1985 | Klaue |
| 4,503,847 A | 3/1985 | Mouradian |
| 4,506,662 A | 3/1985 | Anapliotis |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,630,601 A | 12/1986 | Harder et al. |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,733,654 A | 3/1988 | Marino |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,828,492 A | 5/1989 | Agnone |
| 4,867,144 A | 9/1989 | Karas et al. |
| 4,892,093 A | 1/1990 | Zarnowski et al. |
| 4,893,619 A | 1/1990 | Dale et al. |
| 4,896,661 A | 1/1990 | Bogert et al. |
| 4,903,691 A | 2/1990 | Heinl |
| 4,905,679 A | 3/1990 | Morgan |
| 4,915,092 A | 4/1990 | Firica et al. |
| 4,923,471 A | 5/1990 | Morgan |
| 4,926,847 A | 5/1990 | Luckman |
| 4,930,494 A | 6/1990 | Takehana et al. |
| 4,943,292 A | 7/1990 | Foux |
| 4,947,942 A | 8/1990 | Lightle et al. |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karás et al. |
| 4,966,599 A | 10/1990 | Pollock |
| 4,973,332 A | 11/1990 | Kummer |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,013,314 A | 5/1991 | Firica et al. |
| 5,013,315 A | 5/1991 | Barrows |
| 5,015,248 A | 5/1991 | Burstein et al. |
| 5,021,056 A | 6/1991 | Hofmann et al. |
| 5,035,697 A | 7/1991 | Frigg |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,116,335 A | 5/1992 | Hannon et al. |
| 5,129,899 A | 7/1992 | Small et al. |
| 5,133,718 A | 7/1992 | Mao |
| 5,135,527 A | 8/1992 | Ender |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |

(56) References Cited

U.S. PATENT DOCUMENTS

| | | |
|---|---|---|
| 5,190,544 A | 3/1993 | Chapman et al. |
| 5,190,545 A | 3/1993 | Corsi et al. |
| 5,197,966 A | 3/1993 | Sommerkamp |
| 5,201,736 A | 4/1993 | Strauss |
| 5,201,737 A | 4/1993 | Leibinger et al. |
| 5,234,431 A | 8/1993 | Keller |
| 5,254,119 A | 10/1993 | Schreiber |
| 5,261,908 A | 11/1993 | Campbell, Jr. |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,318,566 A | 6/1994 | Miller |
| 5,356,410 A | 10/1994 | Pennig |
| 5,364,398 A | 11/1994 | Chapman et al. |
| 5,364,399 A | 11/1994 | Lowery et al. |
| 5,380,327 A | 1/1995 | Eggers et al. |
| 5,381,943 A | 1/1995 | Allen et al. |
| 5,387,218 A | 2/1995 | Meswania |
| 5,391,170 A | 2/1995 | McGuire et al. |
| 5,411,514 A | 5/1995 | Fucci et al. |
| 5,413,577 A | 5/1995 | Pollock |
| 5,413,579 A | 5/1995 | Tom Du Toit |
| 5,423,826 A | 6/1995 | Coates et al. |
| 5,431,323 A * | 7/1995 | Smith ............... A61B 17/0682 227/177.1 |
| 5,443,483 A | 8/1995 | Kirsch |
| 5,443,516 A | 8/1995 | Albrektsson et al. |
| 5,464,407 A | 11/1995 | McGuire |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,490,819 A | 2/1996 | Nicholas et al. |
| 5,522,902 A | 6/1996 | Yuan et al. |
| 5,527,311 A | 6/1996 | Procter et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,571,103 A | 11/1996 | Bailey |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,603,715 A | 2/1997 | Kessler |
| 5,607,426 A | 3/1997 | Ralph et al. |
| 5,643,261 A | 7/1997 | Schäfer et al. |
| 5,643,265 A | 7/1997 | Errico et al. |
| 5,645,599 A | 7/1997 | Samani |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,665 A | 10/1997 | Bryan |
| 5,676,667 A | 10/1997 | Hausman |
| 5,681,313 A | 10/1997 | Diez |
| 5,690,660 A | 11/1997 | Kauker et al. |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,725,536 A | 3/1998 | Oberlin et al. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,797,918 A | 8/1998 | McGuire et al. |
| 5,807,396 A | 9/1998 | Raveh |
| 5,810,823 A | 9/1998 | Klaue et al. |
| 5,810,824 A | 9/1998 | Chan |
| 5,814,047 A | 9/1998 | Emilio et al. |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,888,247 A | 3/1999 | Benetti |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |
| 5,941,878 A | 8/1999 | Medoff |
| 5,951,557 A | 9/1999 | Luter |
| 5,951,575 A * | 9/1999 | Bolduc ............... A61B 17/062 606/139 |
| 5,954,722 A | 9/1999 | Bono |
| 5,964,763 A | 10/1999 | Incavo et al. |
| 5,968,046 A | 10/1999 | Castleman |
| 5,968,047 A | 10/1999 | Reed |
| 5,973,223 A | 10/1999 | Tellman et al. |
| 6,001,099 A | 12/1999 | Huebner |
| 6,004,323 A | 12/1999 | Park et al. |
| 6,004,353 A | 12/1999 | Masini |
| 6,007,535 A | 12/1999 | Rayhack et al. |
| 6,007,538 A | 12/1999 | Levin |
| 6,022,350 A | 2/2000 | Ganem |
| 6,027,504 A | 2/2000 | McGuire |
| 6,053,915 A | 4/2000 | Bruchmann |
| 6,053,918 A | 4/2000 | Spievack |
| 6,069,040 A | 5/2000 | Miles et al. |
| 6,077,266 A | 6/2000 | Medoff |
| 6,077,271 A | 6/2000 | Huebner et al. |
| 6,093,188 A | 7/2000 | Murray |
| 6,096,040 A | 8/2000 | Esser |
| 6,096,042 A | 8/2000 | Herbert |
| 6,113,603 A | 9/2000 | Medoff |
| 6,117,139 A | 9/2000 | Shino |
| 6,117,160 A | 9/2000 | Bonutti |
| 6,123,709 A | 9/2000 | Jones |
| 6,129,728 A | 10/2000 | Schumacher et al. |
| 6,129,730 A | 10/2000 | Bono et al. |
| 6,139,548 A | 10/2000 | Errico |
| 6,152,927 A | 11/2000 | Farris et al. |
| 6,159,213 A | 12/2000 | Rogozinski |
| 6,179,839 B1 | 1/2001 | Weiss et al. |
| 6,183,475 B1 | 2/2001 | Lester et al. |
| 6,189,422 B1 | 2/2001 | Stihl |
| 6,193,721 B1 | 2/2001 | Michelson |
| 6,197,028 B1 | 3/2001 | Ray et al. |
| 6,197,037 B1 | 3/2001 | Hair |
| 6,221,073 B1 | 4/2001 | Weiss et al. |
| 6,224,602 B1 | 5/2001 | Hayes |
| 6,228,087 B1 | 5/2001 | Fenaroli et al. |
| 6,235,033 B1 | 5/2001 | Brace et al. |
| 6,235,034 B1 | 5/2001 | Bray |
| 6,238,396 B1 | 5/2001 | Lombardo |
| 6,258,092 B1 | 7/2001 | Dail |
| 6,261,291 B1 | 7/2001 | Talaber et al. |
| 6,273,889 B1 | 8/2001 | Richelsoph |
| 6,280,446 B1 | 8/2001 | Blackmore |
| 6,283,969 B1 | 9/2001 | Grusin et al. |
| 6,290,703 B1 | 9/2001 | Ganem |
| 6,302,883 B1 | 10/2001 | Bono |
| 6,302,884 B1 | 10/2001 | Wellisz et al. |
| 6,302,887 B1 | 10/2001 | Spranza et al. |
| 6,306,136 B1 | 10/2001 | Baccelli |
| 6,312,431 B1 | 11/2001 | Asfora |

(56) References Cited

U.S. PATENT DOCUMENTS

| | | |
|---|---|---|
| 6,315,779 B1 | 11/2001 | Morrison et al. |
| 6,322,562 B1 | 11/2001 | Wolter |
| 6,325,803 B1 | 12/2001 | Schumacher et al. |
| 6,331,179 B1 | 12/2001 | Freid et al. |
| 6,335,041 B1 | 1/2002 | Baur et al. |
| 6,336,927 B2 | 1/2002 | Rogozinski |
| 6,338,734 B1 | 1/2002 | Burke et al. |
| 6,342,055 B1 | 1/2002 | Eisermann et al. |
| 6,342,075 B1 | 1/2002 | MacArthur |
| 6,355,036 B1 | 3/2002 | Nakajima |
| 6,355,042 B2 | 3/2002 | Winquist et al. |
| 6,358,250 B1 | 3/2002 | Orbay |
| 6,364,881 B1 | 4/2002 | Apgar et al. |
| 6,364,882 B1 | 4/2002 | Orbay |
| 6,364,883 B1 | 4/2002 | Santilli |
| 6,379,354 B1 | 4/2002 | Rogozinski |
| 6,379,359 B1 | 4/2002 | Dahners |
| 6,379,364 B1 | 4/2002 | Brace et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,436,103 B1 | 8/2002 | Suddaby |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,503,250 B2 | 1/2003 | Paul |
| 6,508,819 B1 | 1/2003 | Orbay |
| 6,514,274 B1 | 2/2003 | Boucher et al. |
| 6,520,965 B2 | 2/2003 | Chervitz et al. |
| 6,527,775 B1 | 3/2003 | Warburton |
| 6,547,790 B2 | 4/2003 | Harkey, III et al. |
| 6,533,789 B1 | 5/2003 | Hall, IV et al. |
| 6,565,570 B2 | 5/2003 | Sterett et al. |
| 6,572,620 B1 | 6/2003 | Schon et al. |
| 6,592,578 B2 | 7/2003 | Henniges et al. |
| 6,595,993 B2 | 7/2003 | Donno et al. |
| 6,602,255 B1 | 8/2003 | Campbell et al. |
| 6,623,486 B1 | 9/2003 | Weaver et al. |
| 6,623,487 B1 | 9/2003 | Goshert |
| 6,660,010 B2 * | 12/2003 | Gellman ............ A61B 17/0401 606/104 |
| 6,663,642 B2 | 12/2003 | Beyar et al. |
| 6,682,531 B2 | 1/2004 | Winquist et al. |
| 6,682,533 B1 | 1/2004 | Dinsdale et al. |
| 6,689,139 B2 | 2/2004 | Horn |
| 6,695,846 B2 | 2/2004 | Richelsoph et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,730,091 B1 | 5/2004 | Pfefferle et al. |
| 6,736,819 B2 | 5/2004 | Tipirneni |
| 6,767,351 B2 | 7/2004 | Orbay et al. |
| 6,793,658 B2 | 9/2004 | LeHuec et al. |
| 6,821,278 B2 | 11/2004 | Frigg et al. |
| 6,858,031 B2 | 2/2005 | Morrison et al. |
| 6,863,694 B1 | 3/2005 | Boyce et al. |
| 6,866,665 B2 | 3/2005 | Orbay |
| 6,893,444 B2 | 5/2005 | Orbay |
| 6,923,813 B2 * | 8/2005 | Phillips ............... A61B 17/1604 606/192 |
| 6,955,677 B2 | 10/2005 | Dahners |
| 6,974,461 B1 | 12/2005 | Wolter |
| 7,011,659 B2 | 3/2006 | Lewis et al. |
| 7,070,600 B2 | 7/2006 | Silverman |
| 7,077,844 B2 | 7/2006 | Michelson |
| 7,131,840 B2 | 11/2006 | Constantino |
| 7,413,543 B2 * | 8/2008 | Banik ....................... A61B 1/04 600/129 |
| 7,422,585 B1 | 9/2008 | Eggers et al. |
| 7,442,195 B1 | 10/2008 | Behrens |
| 7,585,300 B2 | 9/2009 | Cha |
| 7,635,365 B2 | 12/2009 | Ellis et al. |
| 7,666,189 B2 | 2/2010 | Gerber et al. |
| 7,682,378 B2 | 3/2010 | Truckai et al. |
| 7,695,501 B2 | 4/2010 | Ellis et al. |
| 7,695,502 B2 | 4/2010 | Orbay et al. |
| 7,699,203 B2 | 4/2010 | McBride et al. |
| 7,727,264 B2 | 6/2010 | Orbay et al. |
| 7,731,718 B2 | 6/2010 | Schwammberger et al. |
| 7,842,041 B2 | 11/2010 | Liu et al. |
| 8,568,417 B2 | 10/2013 | Petrzelka et al. |
| 8,632,573 B2 | 1/2014 | Ellis et al. |
| 9,237,910 B2 | 1/2016 | Seykora et al. |
| 2001/0011172 A1 | 8/2001 | Orbay et al. |
| 2002/0004660 A1 | 1/2002 | Henniges et al. |
| 2002/0032446 A1 | 3/2002 | Orbay |
| 2002/0055741 A1 | 5/2002 | Schlapfer et al. |
| 2002/0128654 A1 | 9/2002 | Steger et al. |
| 2002/0143336 A1 | 10/2002 | Hearn |
| 2002/0143337 A1 | 10/2002 | Orbay et al. |
| 2002/0143338 A1 | 10/2002 | Orbay et al. |
| 2002/0147453 A1 | 10/2002 | Gambale |
| 2002/0151899 A1 | 10/2002 | Bailey et al. |
| 2002/0156474 A1 | 10/2002 | Wack et al. |
| 2002/0177852 A1 | 11/2002 | Chervitz et al. |
| 2002/0183752 A1 | 12/2002 | Steiner et al. |
| 2003/0040748 A1 | 2/2003 | Aikins et al. |
| 2003/0055429 A1 | 3/2003 | Ip et al. |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner et al. |
| 2004/0116930 A1 | 6/2004 | O'Driscoll et al. |
| 2004/0127901 A1 | 7/2004 | Huebner et al. |
| 2004/0127903 A1 | 7/2004 | Schlapfer et al. |
| 2004/0127904 A1 | 7/2004 | Konieczynski et al. |
| 2004/0153073 A1 | 8/2004 | Orbay |
| 2004/0186472 A1 | 9/2004 | Lewis et al. |
| 2004/0193164 A1 | 9/2004 | Orbay |
| 2004/0193165 A1 | 9/2004 | Orbay |
| 2004/0220566 A1 | 11/2004 | Bray |
| 2004/0220577 A1 | 11/2004 | Cragg et al. |
| 2004/0260291 A1 | 12/2004 | Jensen |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0015089 A1 | 1/2005 | Young et al. |
| 2005/0015090 A1 | 1/2005 | Silverman |
| 2005/0049593 A1 | 3/2005 | Duong et al. |
| 2005/0065520 A1 | 3/2005 | Orbay |
| 2005/0065522 A1 | 3/2005 | Orbay |
| 2005/0065523 A1 | 3/2005 | Orbay |
| 2005/0065524 A1 | 3/2005 | Orbay |
| 2005/0065528 A1 | 3/2005 | Orbay |
| 2005/0070902 A1 | 3/2005 | Medoff |
| 2005/0085818 A1 | 4/2005 | Huebner |
| 2005/0085819 A1 | 4/2005 | Ellis et al. |
| 2005/0131413 A1 | 6/2005 | O'Driscoll et al. |
| 2005/0159747 A1 | 7/2005 | Orbay |
| 2005/0165395 A1 | 7/2005 | Orbay et al. |
| 2005/0165400 A1 | 7/2005 | Fernandez |
| 2005/0171544 A1 | 8/2005 | Falkner, Jr. |
| 2005/0182405 A1 | 8/2005 | Orbay et al. |
| 2005/0182406 A1 | 8/2005 | Orbay et al. |
| 2005/0187551 A1 | 8/2005 | Orbay et al. |
| 2005/0192578 A1 | 9/2005 | Horst |
| 2005/0234458 A1 | 10/2005 | Huebner |
| 2005/0261684 A1 | 11/2005 | Shaolian et al. |
| 2006/0058796 A1 | 3/2006 | Hartdegen et al. |
| 2006/0085000 A1 | 4/2006 | Mohr et al. |
| 2006/0100623 A1 | 5/2006 | Pennig |
| 2006/0150986 A1 | 7/2006 | Roue et al. |
| 2007/0043367 A1 | 2/2007 | Lawrie |
| 2007/0043368 A1 | 2/2007 | Lawrie et al. |
| 2007/0083202 A1 | 4/2007 | Eli Running et al. |
| 2007/0123883 A1 | 5/2007 | Ellis et al. |
| 2007/0185493 A1 | 8/2007 | Feibel et al. |

(56) References Cited

U.S. PATENT DOCUMENTS

| | | |
|---|---|---|
| 2007/0213727 A1 | 9/2007 | Bottlang et al. |
| 2008/0178712 A1 | 7/2008 | Brown |
| 2008/0243136 A1 | 10/2008 | Prager et al. |
| 2008/0249481 A1 | 10/2008 | Crainich et al. |
| 2008/0269768 A1 | 10/2008 | Schwager et al. |
| 2009/0005822 A1 | 1/2009 | Kitchens |
| 2009/0023988 A1 | 1/2009 | Korner et al. |
| 2009/0036930 A1 | 2/2009 | Allison |
| 2009/0069812 A1 | 3/2009 | Gillard et al. |
| 2009/0118768 A1 | 5/2009 | Sixto, Jr. et al. |
| 2009/0157081 A1 | 6/2009 | Homan et al. |
| 2009/0177240 A1 | 7/2009 | Perez |
| 2009/0188965 A1 | 7/2009 | Levin et al. |
| 2009/0259107 A1 | 10/2009 | Crenshaw et al. |
| 2010/0001038 A1 | 1/2010 | Levin et al. |
| 2010/0234896 A1 | 9/2010 | Lorenz et al. |
| 2010/0274245 A1 | 10/2010 | Gonzalez-Hernandez |
| 2010/0331844 A1 | 12/2010 | Ellis et al. |
| 2010/0331892 A1 | 12/2010 | Fell et al. |
| 2011/0152867 A1 | 6/2011 | Petrzelka et al. |
| 2013/0072936 A1* | 3/2013 | To ..................... A61B 17/1671 606/79 |

FOREIGN PATENT DOCUMENTS

| | | |
|---|---|---|
| CH | 576249 A5 | 6/1976 |
| CH | 611147 A5 | 5/1979 |
| CN | 201755247 U | 3/2011 |
| DE | 2515430 A1 | 11/1975 |
| DE | 3808937 A1 | 10/1989 |
| DE | 9115341 U1 | 2/1992 |
| DE | 4201531 A1 | 7/1993 |
| DE | 4343117 A1 | 6/1995 |
| EP | 0029752 A1 | 6/1981 |
| EP | 0094039 A1 | 11/1983 |
| EP | 0179695 A1 | 4/1986 |
| EP | 0053999 B1 | 3/1987 |
| EP | 0410309 A1 | 1/1991 |
| EP | 0415837 A2 | 3/1991 |
| EP | 0362049 B1 | 5/1992 |
| EP | 0561295 A1 | 9/1993 |
| EP | 0471418 B1 | 6/1995 |
| EP | 1250892 A2 | 10/2002 |
| FR | 742618 | 3/1933 |
| FR | 2211851 | 7/1974 |
| FR | 2254298 | 7/1975 |
| FR | 2367479 | 5/1978 |
| FR | 2405705 | 5/1979 |
| FR | 2405706 | 5/1979 |
| FR | 2406429 | 5/1979 |
| FR | 2416683 | 9/1979 |
| FR | 2472373 | 7/1981 |
| FR | 2674118 A1 | 9/1992 |
| GB | 2245498 A | 1/1992 |
| GB | 2331244 A | 5/1999 |
| GB | 2435429 A | 8/2007 |
| JP | S47-44985 | 5/1972 |
| JP | S64-03285 A | 2/1989 |
| JP | H05-146502 A | 6/1993 |
| JP | H06-3551 Y2 | 2/1994 |
| JP | 2002-542875 A | 12/2002 |
| JP | 2007503885 A | 3/2007 |
| SU | 610518 | 6/1978 |
| SU | 718097 | 2/1980 |
| SU | 862937 | 9/1981 |
| SU | 874044 | 10/1981 |
| SU | 897233 | 1/1982 |
| SU | 921553 | 4/1982 |
| SU | 1049054 A | 10/1983 |
| SU | 1130332 A | 12/1984 |
| SU | 1192806 A | 11/1985 |
| SU | 1223901 A | 4/1986 |
| SU | 1225556 A | 4/1986 |
| SU | 1544406 A1 | 2/1990 |
| SU | 1630804 A1 | 2/1991 |
| SU | 1644932 A1 | 4/1991 |
| SU | 1683724 A1 | 10/1991 |
| SU | 1711859 A1 | 2/1992 |
| SU | 1734715 A1 | 5/1992 |
| WO | 8201645 A1 | 5/1982 |
| WO | 8702572 A1 | 5/1987 |
| WO | 8803781 A1 | 6/1988 |
| WO | 9505782 A1 | 3/1995 |
| WO | 9629948 A1 | 10/1996 |
| WO | 9747251 A1 | 12/1997 |
| WO | 9922089 A1 | 5/1999 |
| WO | 0062693 A1 | 10/2000 |
| WO | 0121083 A1 | 3/2001 |
| WO | 0162136 A2 | 8/2001 |
| WO | 0203882 A2 | 1/2002 |
| WO | 03105712 A2 | 12/2003 |
| WO | 2007092813 A2 | 8/2007 |
| WO | 2007109436 A2 | 9/2007 |
| WO | 2009086402 A1 | 7/2009 |

OTHER PUBLICATIONS

Peine et al, "Comparison of Three Different Plating Techniques for the Dorsum of the Distal Radius: A Biomechanical Study", Journal of Hand Surgery, vol. 25A, No. 1, pp. 29-33, Jan. 2000.

Young, "Outcome Following Nonoperative Treatment of Displaced Distal Radius Fractures in Low-Demand Patients Older Than 60 Years", Journal of Hand Surgery, vol. 25A, No. 1, pp. 19-28, Jan. 2000.

Putnam et al., "Distal Radial Metaphyseal Forces in an Extrinsic Grip Model: Implications for Postfracture Rehabilitation", Journal of Hand Surgery, vol. 25A, No. 3, pp. 469-475, May 2000.

Surfix Technologies, Single Units Osteosynthesis brochure, Sep. 2000.

Lardinois et al., "Pulmonary Function Testing After Operative Stabilisation of the Chest Wall for Flail Chest", European Journal of Cardio-thoracic Surgery (2001) 20:496-501.

Ng et al., "Operative Stabilisation of Painful Non-united Multiple Rib Fractures", Injury (2001) 32:637-639.

Synthes (USA), Titanium Distal Radius Plates description page, 2001.

Wright Medical Technology, Inc., Locon-T Distal Radius Plating System case study and surgical method, 2001.

TriMed Inc., TriMed Wrist Fixation System Internet description pages, 2001.

Slater et al., "Operative Stabilization of Flail Chest Six Years After Injury", Annals of Thoracic Surgery Aug. 2001:600-601.

Sanchez-Sotelo et al., "Principle-Based Internal Fixation of Distal Humerus Fractures, Techniques in Hand & Upper Extremity Surgery", vol. 5, No. 4, pp. 179-187, Dec. 2001.

Abel et al., "An Axially Mobile Plate for Fracture Fixation", Internal Fixation in Osteoporotic Bone, pp. 279-283, 2002.

An, Y.H., Internal Fixation in Osteoporotic Bone, pp. 82-83, 2002.

Konrath et al., "Open Reduction and Internal Fixation of Unstable Distal Radius Fractures: Results Using the Trimed Fixation System", Journal of Orthopaedic Trauma, vol. 16, No. 8, pp. 578-585, 2002.

Mizuho Co., Ltd., Jplate Diaphysis Plates for Japanese brochure, 2002.

Synthes (USA), 3.5 mm LCP™ Proximal Humerus Plate technique guide, 2002.

Tanaka et al., "Surgical Stabilization or Internal Pneumatic Stabilization? A Prospective Randomized Study of Management of Severe Flail Chest Patients", Journal of Trauma (2002) 52:727-732.

Sing et al., "Thoracoscopic Resection of Painful Multiple Rib Fractures: Case Report" The Journal of Trauma, vol. 52, No. 2, pp. 391-392, 2002.

Tornetta, Distal Radius Fracture, Journal of Orthopaedic Trauma, vol. 16, No. 8, pp. 608-611, 2002.

Wright Medical Technology, Inc., Locon-T Distal Radius Plating System brochure, 2002.

Zimmer, Inc., Periarticular Plating System brochure, 2002.

(56) References Cited

OTHER PUBLICATIONS

Acumed Inc., Congruent Plate System— The Mayo Clinic Congruent Elbow Plates brochure, May 7, 2002.
Acumed Inc., Modular Hand System brochure, Aug. 2002.
Acumed Inc., Modular Hand System brochure, Sep. 2002.
Harvey et al., "The Use of a Locking Custom Contoured Blade Plate for Peri-Nonunions", Injury, Int. J. Care Injured, vol. 34, pp. 111-116, 2003.
Chin et al., "Salvage of Distal Tibia Metaphyseal Nonunions With the 90° Cannulated Blade Plate", Clinical Orthopaedics and Related Research, No. 409, pp. 241-249, 2003.
Hooker et al., Fixation of Unstable Fractures of the Volar Rim of the Distal Radius with a Volar Buttress Pin®, 2003.
Rozental et al., Functional Outcome and Complications Following Two Types of Dorsal Plating for Unstable Fractures of the Distal Part of the Radius, Journal of Bone and Joing Surgery, vol. 85, No. 10, pp. 1956-1960, 2003 (abstract only).
Osada et al.., "Comparison of Different Distal Radius Dorsal and Volar Fracture Fixation Plates: A Biomechanical Study", Journal of Hand Surgery, vol. 28A, No. 1, pp. 94-104, Jan. 2003.
Turner et al., Tendon Function and Morphology Related to Material and Design of Plates for Distal Radius Fracture Fixation: Canine Forelimb Model, Orthopaedic Research Society, Feb. 2003.
Erothitan Titanimplantate AG, Titanium Wire Plate Osteosynthesis System According to Dr. Gahr internet printout, print date Feb. 6, 2003.
Simic, "Fractures of the Distal Aspect of the Radius: Changes in Treatment Over the Past Two Decades", Journal of Bone and Joint Surgery, vol. 85-A, No. 3, pp. 552-564, Mar. 2003.
Leung et al., "Palmar Plate Fixation of AO Type C2 Fracture of Distal Radius Using a Locking Compression Plate—A Biomechanical Study in a Cadaveric Model", Journal of Hand Surgery, vol. 28B, No. 3, pp. 263-266, Jun. 2003.
Martin GmbH & Co. KG, Bilder internet printout, print date Sep. 5, 2003.
Mayberry, "Absorbable Plates for Rib Fracture Repair: Preliminary Experience", Journal of Trauma Injury, Infection and Critical Care. vol. 55, No. 5, pp. 835-839, Nov. 2003.
Moore et al., Clinically Oriented Anatomy, Fourth Edition, pp. 70-71, 2004.
Orthocopia, LLC, Synthes Volar Distal Radius Locking Plate Internet description page, 2004.
Ruch et al., "Results of Palmar Plating of the Lunate Facet Combined with External Fixation for the Treatment of High-Energy Compression Fractures of the Distal Radius", J. Orthop. Trauma, Vo. 18, No. 1, pp. 28-33, Jan. 2004.
Sanatmetal, Rib Securing Clamped Plate, internet printout, Sep. 2004 <http:/lwww.sanatmetal.hu/catalog/pict/1_5_89a_1.jpg >.
Zespol Bone Plates, in Mikromed—Catalogue 2004 (Nov. 2004), original website <http://www.mikromed.p1/katalog/Main/main_eng.htm> and < http://www.mikromed.pl/katalog/zespol_eng/plytki.htm >, viewable via the Internet Archive Wayback Machine < http://replay.waybackmachine.org/ 20070830023439/http://www.mikromed.pl/katalog/zespol_eng/plytki.htm >.
Zespol Bone Screws, in Mikromed—Catalogue 2004 (Nov. 2004), original website <http:llwww.mikromed.pl/katalog/Main/main_eng.htm> and < http://www.mikromed.pl/katalog/zespol_eng/wkrety.htm >, viewable via the Internet Archive Wayback Machine < http://replay.waybackmachine.org/ 20050226124226/http://www.mikromed.pl/katalog/zespol_eng/wkrety.htm >.
Stryker SmartLock Locking Screw Technology, advertisement, The Journal of Hand Surgery, vol. 30A, No. 1, Jan. 2005.
DVO Extremity Solutions, Mlfx Dorsal IM Plate, brochure, Sep. 2005.
Engel, C., Krieg, J.C., Madey, S.M., Long, W.B., and Bottlang, M., 2005, "Operative Chest Wall Fixation with Ostesynthesis Plates," Journal of Trauma, 58(1), pp. 181-186.
Legacy Biomechanics Laboratory, Applied Research, Jan. 2006, original website <http://www.biomechresearch.org/sling.html>, viewable via the Internet Archive Wayback Machine <http://replay.waybackmachine.org/ 20060320091922/http://www.biomechresearch.org/sling.html>.
Osteomed, images of Resorable Plates, Feb. 2006 <http://www.osteomedcorp.com/images/library/resorbfixation.gif>.
Nirula, R., Diaz, J.J., Trunkey, D.D., and Mayberry, J.C., 2009, "Rib Fracture Repari: Indications, Technical Issues, and Future Directions," World Journal of Surgery, 33(1): pp. 14-22.
AO Foundation, TK System: Innovations, Dec. 2011.
Acromio-Clavicular Plates description page, author and date unknown.
Codman & Shurtleff, Inc., Zuelzer Hook Plates description page, p. 808, undated.
Esser Complete Distal Radius Plate System, undated.
Esser, Proximal Humerus Fractures operative technique, undated.
Kinetics Medical Incorporated, Spider™ and Mini-Spider™ Limited Wrist Fusion System brochure, undated.
Kinetics Medical Incorporated, Spider™ Limited Wrist Fusion System brochure, undated.
US Implants, VAL Plate description page, undated.
Zimmer, Inc., ECT Internal Fracture Fixation brochure, undated.
Zimmer, Inc., ECT Internal Fracture Fixation System order information brochure, undated.
Zimmer, Inc., NexGen Osteotomy System (OS) surgical technique brochure, undated.
DePuy, Inc., McBride S.M.O. Stainless Steel Bone Plates brochure, 1943.
Vitallium, Bone Plates brochure, Mar. 1948.
Moore et al., "Operative stabilization of nonpenetrating chest injuries", The Journal of Thoracic and Cardiovascular Surgery, vol. 70, No. 4, pp. 619-630, 1975.
Tarazona et al., "Surgical stabilization of traumatic flail chest", pp. 521-527, 1975.
Thomas et al., "Operative stabilization for flail chest after blunt trauma", The Journal of Thoracic and Cardiovascular Surgery, vol. 75, No. 6, pp. 793-801, 1978.
Trunkey, "Chest Wall Injuries", Cerviothoracic Trauma, vol. 3. pp. 129-149, 1986.
Klein et al., "Rib Fracture Healing after Osteosynthesis with Wire Mesh Titanium and Screws: A Histological Study in Sheep", Eur Surg Res, vol. 21 pp. 347-354, 1989.
TechMedica, Inc., The Arnett-TMP* Titanium Miniplating System brochure, 1989.
Haasler, "Open Fixation of Flail Chest After Blunt Trauma", The Society of Thoracic Surgeons, pp. 993-995, 1990.
HowMedica Inc., Dupont Distal Humeral Plates brochure, 1990.
Landreneau et al., "Strut Fixation of an Extensive Flail Chest", The Society of Thoracic Surgeons, pp. 473-475, 1991.
Synthes (USA), Biological Plating: A New Concept to Foster Bone Healing, 1991.
Synthes, CMR Matrix: MatrixRIB. Stable fixation of normal and asteoporotic ribs. Techinque Guide, 1991.
TechMedica, Inc., Techmedica Bioengineers Keep Tabs on Your Needs brochure, 1991.
Ace Medical Company, Ace 4.5/5.0 mm Titanium Cannulated Screw and Reconstruction Plate System simplified fracture fixation brochure, 1992.
Ace Medical Company, Ace 4.5/5.0 mm Titanium Cannulated Screw and Reconstruction Plate System surgical technique brochure, 1992.
Beaupre et al., "A Comparison of Unicortical and Bicortical End Screw Attachment of Fracture Fixation Plates", Journal of Orthopaedic Trauma, vol. 6, No. 3, pp. 294-300, 1992.
Ace Medical Company, Ace Titanium 3.5/4.0 mm Screw and Plate System with the Ace 3.5 mm Universal Ribbon CT/MRI compatible fixation brochure, 1994.
Esser, "Treatment of Three- and Four-Part Fractures of the Proximal Humerus with a Modified Cloverleaf Plate", Journal of Orthopaedic Trauma, vol. 8, No. 1, pp. 15-22, 1994.
Amadio, "Open Reduction of Intra-Articular Fractures of the Distal Radius", Fractures of the Distal Radius, pp. 193-202, 1995.
Ducloyer, "Treatment by Plates of Anteriorly Displaced Distal Radial Fractures", Fractures of the Distal Radius, pp. 148-152, 1995.

(56) References Cited

OTHER PUBLICATIONS

Gesensway et al., "Design and Biomechanics of a Plate for the Distal Radius", Journal of Hand Surgery, vol. 20, No. 6, pp. 1021-1027, 1995 (abstract only provided).

Jupiter et al., "Management of Comminuted Distal Radial Fractures", Fractures of the Distal Radius, pp. 167-183, 1995.

Waldemar Link GmbH & Co., May Anatomical Bone Plates: Plates, Bone Screws and Instruments brochure, pp. 3-4 and 10-15, 1995.

Zimmer, Inc., Forte Distal Radial Plate System brochure, 1995.

Ace Medical Company, The Ace Symmetry Titanium Upper Extremity Plates new product release brochure, 1996.

Ace Medical Company, Ace Symmetry Titanium Upper Extremity Plates surgical technique brochure, 1996.

Fernandez et al, Fractures of the Distal Radius: A Practical Approach to Management, pp. 103-188, 1996.

Avanta Orthopaedics, SCS/D Distal Radius Plate System brochure, 1997.

Fitoussi et al., "Treatment of Displaced Intra-Articular Fractures of the Distal End of the Radius With Plates", The Journal of Bone and Joint Surgery, vol. 79, No. 9, pp. 1303-1312, 1997 (abstract only provided).

Synthes (USA), The Titanium Distal Radius Plate, technique guide, 1997.

TriMed Inc., TriMed Wrist Fixation System brochure, 1997.

Synthes, Small Titanium Plates overview page, p. 2a-33, Mar. 1997.

Synthes, Titanium Distal Radius Instrument and Implant Set standard contents description pages, Mar. 1997.

Ring et al., "Prospective Multicenter Trial of a Plate for Dorsal Fixation of Distal Radius Fractures", The Journal of Hand Surgery, vol. 22A, No. 5, pp. 777-784, Sep. 1997.

Avanta Orthopaedics, SCSN Distal Radius Plate Volar brochure, 1998.

Oyarzun et al., "Use of 3.5mm Acetabular Reconstruction Plates for Internal Fixation of Flail Chest Injuries", Section of Cardiothoracic Surgery, pp. 1471-1474, 1998.

Voggenreiter et al., "Operative Chest Wall Stabilization in Flail Chest—Outcomes of Patients With or Without Pulmonary Contusion", American College of Surgeons, pp. 130-138, 1998.

Kolodziej et al., "Biomechanical Evaluation of the Schuhli Nut", Clinical Orthopaedics and Related Research, vol. 347, pp. 79-85, Feb. 1998.

Acumed Inc., Congruent Distal Radius Plate System description, Mar. 4, 1998.

Trumble et al., "Intra-Articular Fractures of the Distal Aspect of the Radius", Journal of Bone and Joint Surgery, vol. 80A, No. 4, pp. 582-600, Apr. 1998.

Kambouroglou etal., "Complications of the AO/ASIF Titanium Distal Radius Plate System (π Plate) in Internal Fixation of the Distal Radius: A Brief Report", Journal of Hand Surgery, vol. 23A, No. 4, pp. 737-741, Jul. 1998.

DePuy Ace, TiMAX Pe.R.I. Small Fragment Upper Extremity description pages, 1999.

Palmer etal., "The Use of Interlocked 'Customised' Blade Plates in the Treatment of Metaphyseal Fractures in Patients with Poor Bone Stock", Injury, Int. J. Care Injured, vol. 31, pp. 187-191, 1999.

Synthes (USA), The Distal Radius Plate Instrument and Implant Set technique guide, 1999.

Tatsumi et al., "Bioabsorable Poly-L-Lactide Costal Coaptation Pins and Their Clinical Application in Thoroacotomy", Original Articles: General Thoracic. pp. 765-768, 1999.

Morgan et al., "Salvage of Tibial Pilon Fractures Using Fusion of the Ankle with a 90° Cannulated Blade Plate: A Preliminary Report", Foot & Ankle International, vol. 20, No. 6, pp. 375-378, Jun. 1999.

Nunley et al., "Delayed Rupture of the Flexor Pollicis Longus Tendon After Inappropriate Placement of the π Plate on the Volar Surface of the Distal Radius", Journal of Hand Surgery, vol. 24, No. 6, pp. 1279-1280, Nov. 1999.

Toby, Scaphoid Protocols Using the Acutrak® Bone Screw System brochure, published by Acumed, Inc., Dec. 1, 1999.

Biomet Orthopedics, Inc., Supracondylar Cable Plate brochure, 2000.

\* cited by examiner

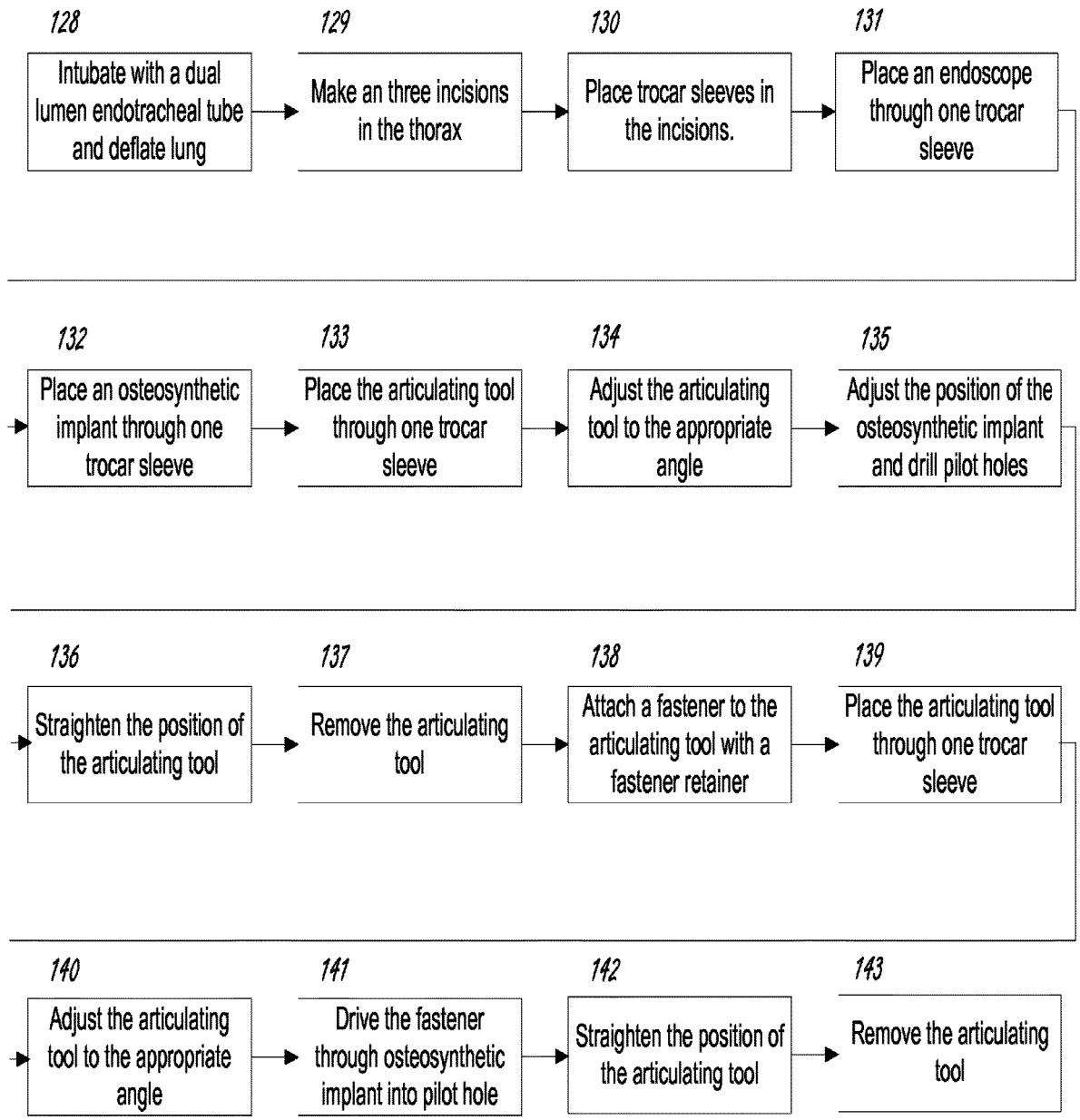

ARTICULATING TOOL AND METHODS OF USING

CROSS-REFERENCES TO PRIORITY APPLICATIONS

This application is a continuation of U.S. patent application Ser. No. 14/065,259, filed Oct. 28, 2013, now U.S. Pat. No. 9,924,986. The '259 application, in turn, is a continuation of U.S. patent application Ser. No. 12/886,474, filed Sep. 20, 2010, now U.S. Pat. No. 8,568,417, which is based upon and claims the benefit under 35 U.S.C. § 119(e) of U.S. Provisional Patent Application Ser. No. 61/288,198, filed Dec. 18, 2009.

Each of these priority applications is incorporated herein by reference in its entirety for all purposes.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract No. FAR 52.227-11 awarded by Dept. of Defense U.S. Army Medical Research and Material Command.

FIELD OF THE INVENTION

The disclosure relates to exemplary embodiments regarding articulating tools to enable drilling or placement of fasteners. More specifically, exemplary embodiments relate to articulating tools for use in endoscopic surgery to place fasteners into bone.

BACKGROUND OF THE INVENTION

Rib fractures are common in trauma patients; about 4-10% of trauma patients have rib fractures, of which 10-15% exhibit paradoxical motion. This condition is painful at best, but also reduces respiratory efficacy; and in extreme cases the fracture endangers the integrity of the lungs or heart due to chest wall instability. Chest wall instability may be treated by sedation of the patient or through artificial respiration, though internal fixation (placement of an osteosynthetic device) is often required.

Despite the benefits of internal fixation, existing procedures are quite invasive. Due to the invasive nature of the surgery many surgeons opt to treat indications with ventilation and analgesia alone. Titanium osteosynthetic plates are perhaps the most prevalent fixation method in the literature. These plates are screwed to the anterior surface of the rib at each fracture site.

SUMMARY OF THE INVENTION

In one aspect, embodiments of an articulating tool may include a housing having a proximal housing end and a distal housing end, an articulating head pivotably connected to the distal housing end by an articulating joint, a controller connected to the proximal housing end, a rotatable drive shaft within the housing having a proximal shaft portion, a medial shaft portion, and a distal shaft portion wherein at least the medial shaft portion is non-rigid, the proximal shaft portion extending through the proximal housing end and the medial shaft portion extending through the articulating joint, and an operable tip connected to the distal shaft portion. The articulating tool may be constructed and arranged to move between at least a first position and a second position by manipulation of the controller, in the first position the articulating head is at a first angle with respect to the longitudinal axis of the housing, and in the second position the longitudinal position of the housing is altered with respect to the rotatable drive shaft wherein the articulating head is at a second angle with respect to the longitudinal axis of the housing. The operable tip may be, but is not limited to, a driver bit or a drill bit.

In other embodiments the articulating tool may include one or more of the following features. The articulating tool may include a fastener retainer connected to the driver tip. The fastener retainer may include a sleeve and a compliant element for retaining a fastener, wherein the compliant element has an inner diameter smaller than an outer diameter of a fastener head. The articulating tool may include an antagonistic spring connected to the articulating joint. The antagonistic spring may be made of a superelastic nickel titanium alloy. The articulating tool may include a motor operably connected to the proximal shaft portion. The articulating tool may include a controller connected to the proximal housing end of the housing, wherein the controller is configured to change between the first position and the second position of the articulating tool. The articulating tool may include a motor operably connected to the controller. The articulating tool may articulate between an angle of less than or equal to about 60°. The articulating head and the housing may have an outer diameter of less than or equal to about 12 millimeters. The articulating tool may be made of bio-inert and autoclavable materials.

In another aspect, embodiments of a method of using an articulating tool may include installing an operable tip at the distal end of the articulating tool, inserting the articulating tool into a body orifice in a mammal, manipulating the controller to adjust the articulating head of the articulating tool, and applying torque to the drive shaft of the articulating tool to engage the operable tip. In one embodiment, the operable tip may be a driver bit with a fastener. In another embodiment, the operable tip may be a drill bit. In one embodiment, the body orifice may be a natural orifice. In another embodiment, the body orifice may be an incision. In another embodiment, the orifice may be a small incision in the thorax. In one embodiment, engaging the operable tip may drive a fastener into body tissue. In another embodiment, engaging the operable tip may drive a fastener into a rib to secure an osteosynthetic implant. In another embodiment, engaging the operable tip may remove material such as in drilling a hole.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 14 illustrates an embodiment of a method of using an articulating tool.

DETAILED DESCRIPTION

Figure 1:
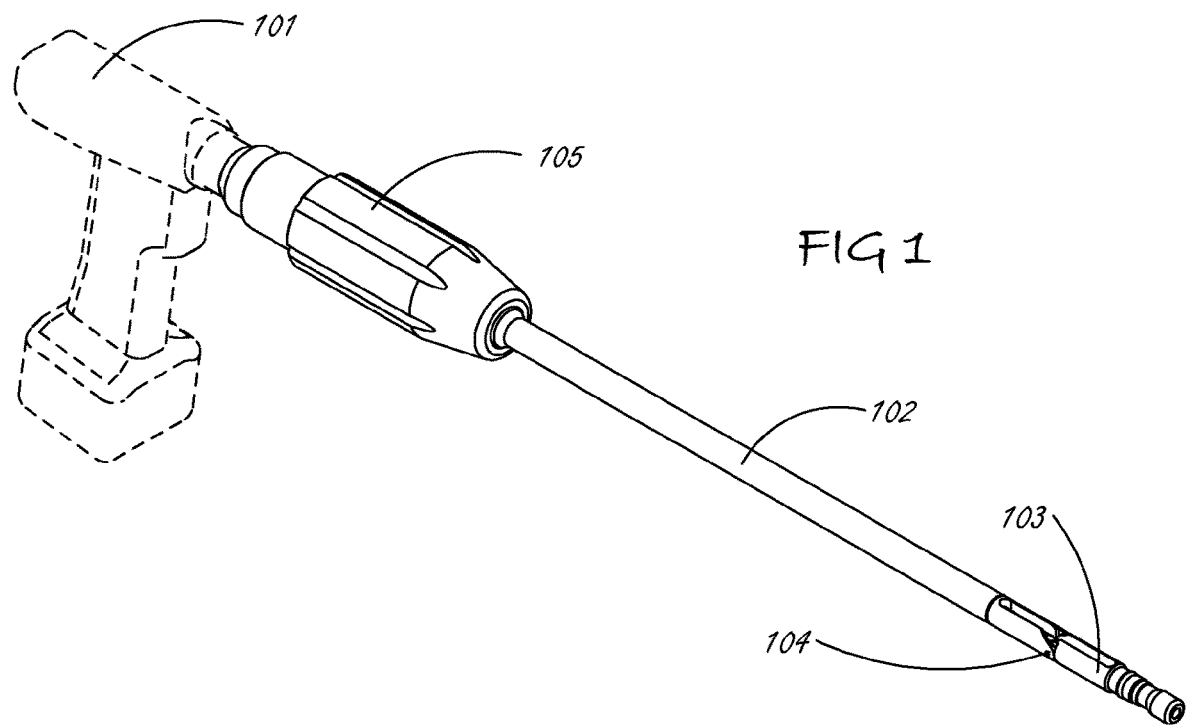
FIG. 1 illustrates an embodiment of an articulating tool.

Described herein are embodiments of articulating tools and methods for conducting thoracoscopic rib fixation. In some embodiments the articulating tool may enter the thoracic cavity through an incision in the thorax of a patient and drill or drive a fastener into the proximal surface of a rib to secure an osteosynthetic implant, for example, but not limited to, an osteosynthetic plate.

Embodiments of the articulating tool may be used to secure osteosynthetic implants to bone during thoracoscopic surgery. More specifically, embodiments of the articulating tool may be used to secure osteosynthetic implants to the posterior cortex of an anterior rib segment, and/or to the anterior cortex of a posterior rib segment, and/or to the medial surface of a lateral rib segment, through a single incision, for minimally invasive internal fixation of rib fractures. The embodiments of the articulating tool may be small enough to be used with a 12 mm trocar sleeve and transmit sufficient torque to fully secure fasteners into bone. An articulating joint at the end of the articulating tool may provide for correct screw alignment at obtuse angles, up to 90° from the articulating tool axis. In some embodiments the articulating tool may facilitate obtuse angles up to 60° from the articulating tool axis. To facilitate obtuse angles up to 60° from the articulating tool axis, a drive shaft having at least a non-rigid intermediate shaft portion may be used to both transmit torque and actuate the articulating joint. The articulating joint may be actuated by changing the longitudinal position of the drive shaft with respect to the rigid housing, or by changing the longitudinal position of the rigid housing with respect to the drive shaft.

The articulating tool may be used for endoscopic placement of fasteners. The articulating tool may be used for endoscopic placement of fasteners, and may provide for minimally invasive internal fixation of rib fractures that may utilize video-assisted thoracic surgery (VATS). Performing internal rib fixation thoracoscopically with the embodiments of the articulating tool may provide a number of advantages. The use of embodiments of the articulating tool may reduce the need for large incisions and separation of musculature required for existing morbid techniques. The use of embodiments of the articulating tool may allow a fracture constrained on the medial surface to be placed in compression during normal respiratory stresses, offering greater mechanical stability and eliminating stress shielding. The use of embodiments of the articulating tool may allow the neurovascular bundle along the inferior edge of each rib to be visible during video-assisted thoracic surgery (VATS) placement, such that the surgeon may avoid nerve contact and associated post-operative patient pain.

Detailed embodiments of the present invention and methods of use are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention.

In one aspect, an embodiment of an articulating tool may include a rigid housing, an articulating head, a drive shaft, and a driver tip. The housing and articulating head may be any shape, length and have any diameter appropriate for performing surgery. In one embodiment the rigid housing and articulating head may have an outer diameter at the widest point sufficient to allow for the housing and articulating head to fit through a trocar sleeve. For example, the housing and articulating head may have an outer diameter at the widest point of about 5-25 mm, 10-20 mm, or 10-15 mm. The housing and articulating head may have a cross-section of any geometric shape, such as but not limited to circular, elliptical, oval, square, triangular, rectangular, octagonal, polygonal, etc. The housing and articulating head may be straight, curved, etc. along the longitudinal axis. The housing and articulating head may be made of any material, such as but not limited to, metals, plastics, polymers, pliable materials, rigid materials, etc., or any combination of the foregoing. In one embodiment the housing and articulating head may be made of a material that may be bio-inert and/or resists high temperatures during autoclave sterilization, such as but not limited to stainless steel, titanium, bio-alloys, and etc. In another embodiment the housing and articulating head may be made of a material that is bio-inert and/or disposable.

The articulating head may be connected to the housing by an articulating joint. The articulating joint may be any type of joint that may allow the articulating head to articulate to a desired angle, such as but not limited to a pivot joint, a sliding joint, a ball and socket joint, a hinge joint, a linkage, a compliant joint, etc. Further, the articulating joint may include more than one joint, such as a series of joints. In one embodiment the articulating joint may be a dual pin hinge joint. More specifically, the hinge pins may be offset slightly from the axis of the actuating element to avoid a kinematic singularity at the straight position. The articulating joint may be made of any material, such as but not limited to, metals, plastics, polymers, pliable materials, rigid materials, etc., or any combination of the foregoing. In one embodiment the articulating joint may be made of a material that may be bio-inert and/or resists high temperatures during autoclave sterilization, such as but not limited to stainless steel, titanium, bio-alloys, etc. In another embodiment the articulating joint may be made of a material that is bio-inert and/or disposable.

The articulating head may articulate to any angle and maintain that angle. In one embodiment, the articulating head may articulate at angles from about 0° to 90°. In another embodiment the articulating head may articulate at angles from about 0° to 60°. It has been determined that based on rib geometry an angle of articulation from about 0° to 60° may allow full access to anterior fractures through a posterior incision.

The length of the articulating head may be directly related to the angle through which the articulating head must articulate. A shorter length of the articulating head may result in improved maneuverability. The length of the articulating head may be any length. The articulating head may be the same length as the housing, may be longer than the length of the housing, or may be shorter than the length of the housing. For endoscopic surgery the length of the articulating head may be about 3 cm to 20 cm. In one embodiment the length of the articulating head may be about 5 cm to 10 cm. In another embodiment the length of the articulating head may be about 6 cm.

The drive shaft may extend through the housing, the articulating joint, and the articulating head. The drive shaft may have a dual purpose to both transmit torque and to actuate the articulating joint. The drive shaft may control the angle of articulation by acting as a tensile element. In one embodiment the articulation of the articulating head may be controlled by altering the longitudinal position of the housing, the articulating head, and/or the articulating joint with respect to the drive shaft. As the longitudinal position of the drive shaft is altered with respect to the housing to increase the tension on the drive shaft the articulating head may be caused to articulate or increase the angle of articulation. For example, to increase the tension on the drive shaft the longitudinal position of the drive shaft may be altered to cause the drive shaft to move away from the articulating end of the articulating tool while keeping the longitudinal position of the housing stationary. As the longitudinal position of the drive shaft is altered with respect to the housing to decrease the tension on the drive shaft the articulating head may be caused to relax, or decrease the angle of articulation. For example, to decrease the tension on the drive shaft the longitudinal position of the drive shaft may be altered to cause the drive shaft to move in the direction of the articulating end of the articulating tool while keeping the longitudinal position of the housing stationary. Additionally, the drive shaft may be rotated simultaneously while the angle of articulation is adjusted.

The drive shaft may be made of any material in the art, such as but not limited to metals, plastics, polymers, pliable materials, rigid materials, flexible materials, etc., or any combination of the foregoing. In one embodiment the drive shaft may be made of a material that may be bio-inert and/or resists high temperatures during autoclave sterilization, such as but not limited to stainless steel, titanium, bio-alloys, etc. In another embodiment the drive shaft may be made of a material that is bio-inert and/or disposable. The drive shaft may be completely flexible, or a combination of flexible portions and rigid portions. The drive shaft may have a flexible portion which extends through the articulating joint to allow for the drive shaft to articulate with the articulating head. The flexible portion could be an element known as a flexible shaft. In another embodiment, the flexible portion of the drive shaft may be composed of an element known as a universal joint or a series of elements known as universal joints. In another embodiment, the flexible portion of the drive shaft may be composed of a gear set.

The articulating tool may further include a slot or aperture in the housing and/or the articulating head. The slot may allow for the drive shaft, when articulated, to move off center at high degrees of articulation. In one embodiment the portion of the drive shaft that articulates is flexible. When the drive shaft is articulated to a high degree of articulation the shaft may move or deflect a small distance from its neutral position or non-actuated position. The slot may allow for the deflecting portion of the drive shaft to move through the slot, thus allowing for full articulation. Additionally, the slot may be covered by a rigid or flexible mechanism to protect the drive shaft.

The articulating tool may further include an antagonistic element on the articulating joint to provide an antagonistic force to the articulating joint. One purpose of the antagonistic element may be to aid in the straightening of the angle of articulation to about 0°. Another purpose of the antagonistic element may be to provide for a more controllable angle of articulation. In one embodiment the antagonistic element may be a spring. The spring may be made of any elastic material capable of providing an antagonistic force and may be either in compression or tension. In one embodiment the antagonistic spring may be made of a super elastic material, such as but not limited to, a nickel titanium alloy. In another embodiment, the antagonistic element may be the flexible portion of the drive shaft.

The articulating tool may further include a controller connected to the proximal end of the housing or drive shaft to control the angle of articulation. In one embodiment the controller may control the longitudinal position of the housing with respect to the drive shaft, thus controlling the angle of articulation. In another embodiment the controller may control the longitudinal position of the drive shaft with respect to the housing, thus controlling the angle of articulation. The controller may be any device capable of altering the longitudinal position of either the housing or the drive shaft with respect to one another, such as but not limited to threaded screws, a gear set, a cam, etc. In one embodiment the controller may be a threaded device that, when turned, alters the longitudinal position of the housing with respect to the drive shaft, which may be held stationary with respect to the housing. In another example the controller may be a threaded device that when turned alters the longitudinal position of the drive shaft with respect to the housing, which may be held stationary with respect to the drive shaft. Further, the controller may be made of any material, such as but not limited to, metals, plastics, polymers, pliable materials, rigid materials, etc., or any combination of the foregoing. In one embodiment the controller may be made of a material that may be bio-inert and/or resists high temperatures during autoclave sterilization, such as but not limited to stainless steel, titanium, bio-alloys, etc. In another embodiment the controller may be made of a material that is bio-inert and/or disposable.

The articulating tool may further include at least one power device for supplying torque to the drive shaft and/or to the controller. Any means for supplying power may be used, such as but not limited to manual, electric, and pneumatic drives. In one embodiment power may be supplied by an electric device such as a DC motor, a DC gear motor, an AC motor, an AC gear motor, etc. The power device used to supply torque to the drive shaft may be capable of having a peak torque of about 1 N and be capable of operating at about 60 RPM with variable speed. The power device may be capable of operating at, for example, about 0-10,000 RPM, 0-1,000 RPM, 0-500 RPM, 0-100 RPM, or 0-60 RPM. In another embodiment, a means may be provided for manually turning the drive shaft, such as but not limited to a twist handle or a lever-screw drive.

The articulating tool may further include an operable tip attached to the drive shaft. The driver tip may be any operable device known in the art such as but not limited to a screwdriver tip, a drill bit, a blade, a socket, an allen tip, a file, etc. In one embodiment the driver tip may be compatible with screws that are about 2.0 mm or 2.3 mm in diameter. The operable device may be capable of easy replacement. The operable tip may be made of any material, such as but not limited to, metals, plastics, polymers, pliable materials, rigid materials, etc., or any combination of the foregoing. In one embodiment the operable tip may be made of a material that may be bio-inert and/or resists high temperatures during autoclave sterilization, such as but not limited to stainless steel, titanium, bio-alloys, etc. In another embodiment the driver tip may be made of a material that is bio-inert and/or disposable.

The articulating tool may further include a fastener retainer for retaining a fastener, screw, nail, staple, etc. on the driver tip prior to insertion into a bone or other material. This can allow the fastener to be placed on the tool prior to insertion into the patient. The fastener retainer may be made of any material, such as but not limited to, metals, plastics, polymers, pliable materials, rigid materials, etc., or any combination of the foregoing. In one embodiment the fastener retainer may be made of a material that may be bio-inert and/or resists high temperatures during autoclave sterilization, such as but not limited to stainless steel, titanium, bio-alloys, etc. In another embodiment the fastener retainer may be made of a material that is bio-inert and/or disposable. The fastener retainer may have a cross-section of any geometric shape, such as but not limited to circular, elliptical, oval, square, triangular, rectangular, octagonal, polygonal, etc. The fastener retainer may be straight, curved, etc. along its longitudinal axis.

The fastener retainer may incorporate any retainer for removably retaining a faster on the driver tip, such as but not limited to compliant rings, ball bearings, teeth, locking sleeves, retaining sleeves, magnetic retainers, etc. The retainer may be an active retainer, which requires the user to release the fastener from the retainer, or a passive means, which does not require the user to release the fastener from the retainer. In one embodiment the fastener retainer may include a compliant element, which may be a ring, having an inner diameter smaller than the outer diameter of the fastener to be retained. The compliant element may retain the fastener and as the fastener fully seats into bone or other material it pulls itself through the compliant ring to a released position. In this manner, the mechanism may be passive and does not require external actuation. The compliant ring may be capable of retaining the fastener even in the presence of reasonable radial forces, such as those on the order of about 10 N. Further, the compliant ring may be capable of retaining the fastener until an axial force of about 10-25 N is applied. In one embodiment, the compliant element may be a separate component of an assembled fastener retainer. In another embodiment, the compliant element may be a feature on a fastener retainer. In one embodiment the compliant ring may be made of a material that may be bio-inert and/or resists high temperatures during autoclave sterilization. In another embodiment the compliant ring may be made of a material that is bio-inert and/or disposable.

In another embodiment the articulating tool may include a handle on which the motor, housing, power supply, and/or controller may be mounted. The handle may be made of any material, such as but not limited to, metals, plastics, polymers, pliable materials, rigid materials, etc., or any combination of the foregoing. In one embodiment the handle may be made of a material that may be bio-inert and/or resists high temperatures during autoclave sterilization, such as but not limited to stainless steel, titanium, bio-alloys, etc. In another embodiment the handle may be made of a material that is bio-inert and/or disposable. Additionally, the handle may include a trigger for controlling the power distributed to the drive shaft and/or controller for controlling the torque applied to the drive shaft and/or the angle of articulation. In one embodiment, the handle may be detachable from the tool and may function as one piece of a modular surgical kit. In another embodiment, the handle may include a means for application of manual torque.

In another embodiment one or more portions of the articulating tool may be capable of being removed and/or disassembled. For example the housing, the articulating head, the controller, the driver tip, the drive shaft, the retention mechanism, etc. may be removed and/or disassembled from the articulating tool. The portions may then be disposed of or sterilized/autoclaved for multiple uses.

Figure 2:
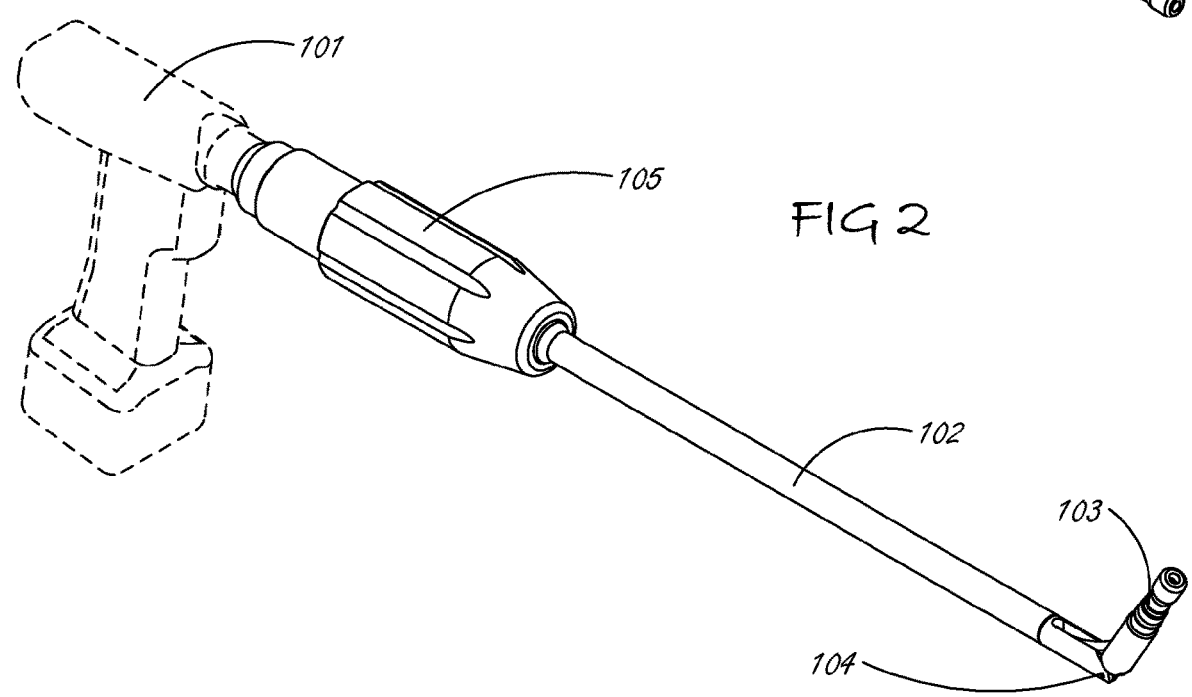
FIG. 2 illustrates the same embodiment of an articulating tool in an articulated position.

Turning to FIG. 1, in one embodiment the articulating tool may attach to a separate battery-powered handpiece 101, may include a housing 102, an articulating head 103, and articulating joint 104. In FIG. 2, the articulating joint 104 may be adjusted, by manipulating the controller 105, to angles between about 0 and 60 degrees. The articulating tool may be made of a material that may be bio-inert and/or resists high temperatures during autoclave sterilization. The housing 102 and the articulating head 103 may have an outer diameter of sufficient size to allow the housing 102 and the articulating head 103 to fit through a 12 mm trocar sleeve.

Figure 3:
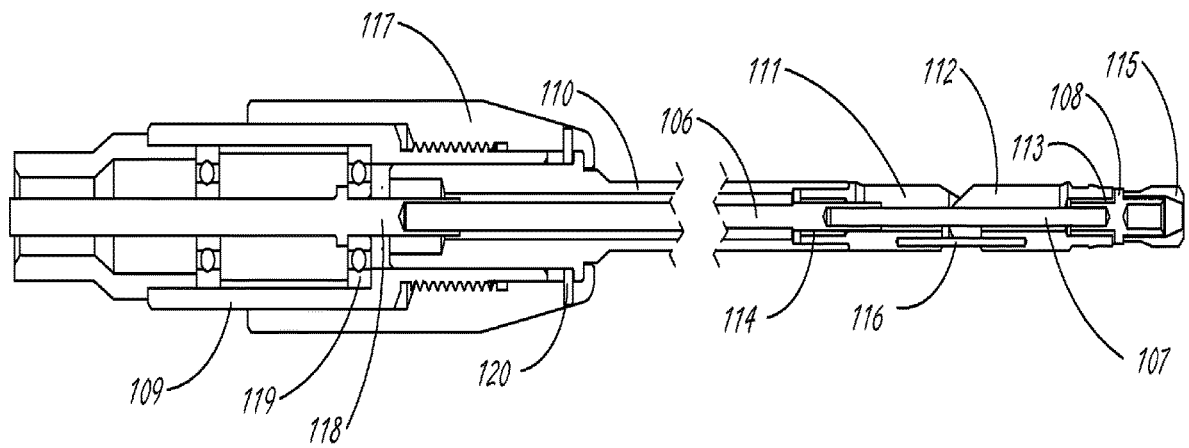
FIG. 3 illustrates a cross-sectional view from one side of the same embodiment of the articulating tool in the straight position.
Figure 4:
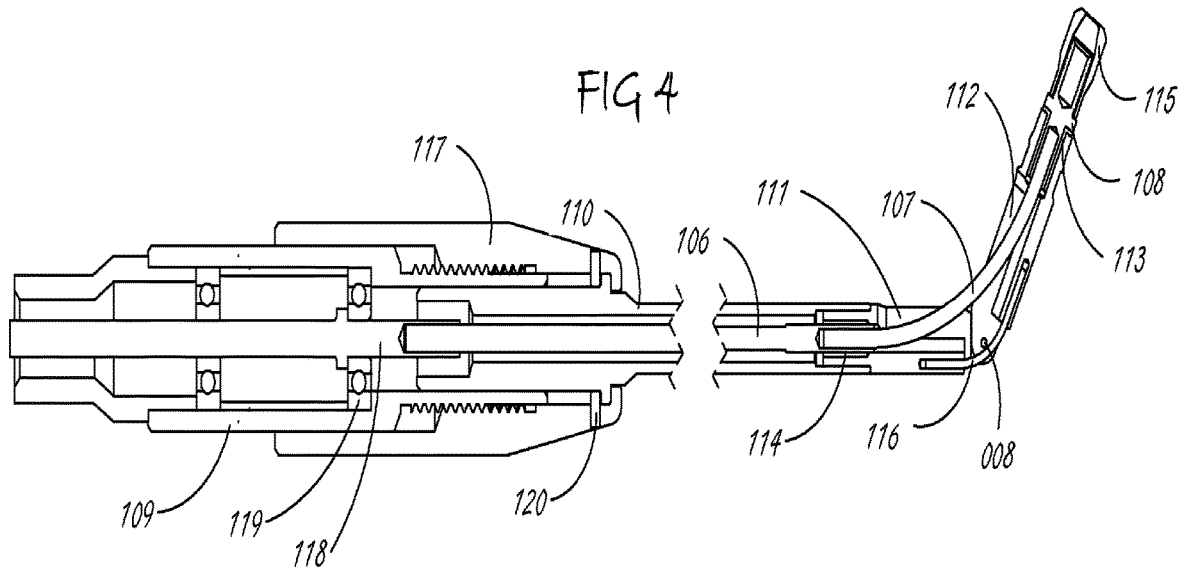
FIG. 4 illustrates a cross-sectional view from one side of the same embodiment of the articulating tool in the articulated position.
Figure 5:
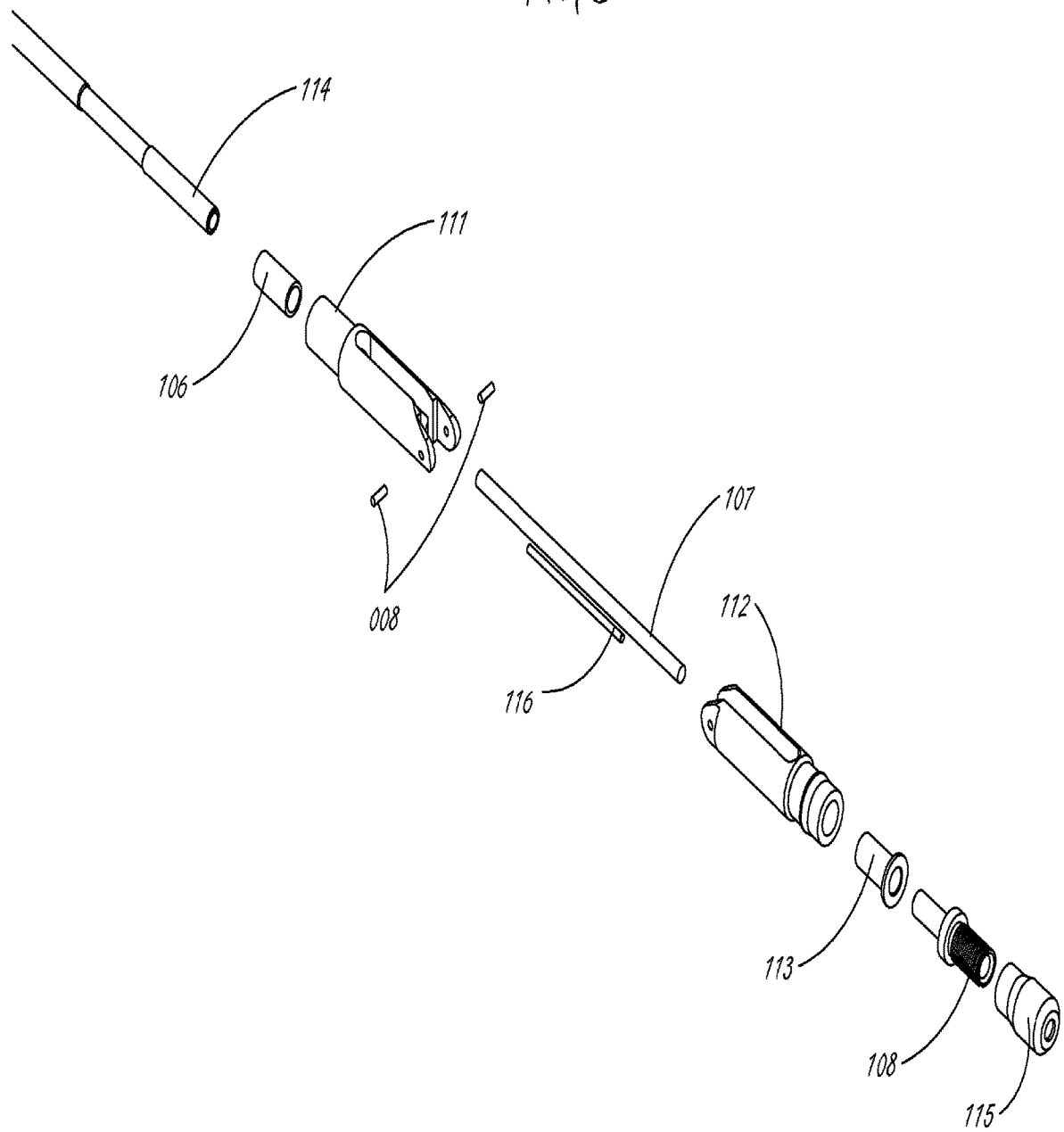
FIG. 5 illustrates an exploded view of the same embodiment of the end of the articulating tool in the straight position.

Referencing FIGS. 3, 4, and 5, the rotatable drive shaft includes a rigid proximal shaft 106, a non-rigid intermediate shaft 107, and a rigid distal shaft 108. In another embodiment, there may be a plurality of shaft sections, each of which may be rigid or non-rigid. In yet another embodiment, there may be as few as one or two shaft sections. The drive shaft assembly extends through the controller housing 109, the tool housing 110, the proximal hinge joint 111, and the distal hinge joint 112. The distal rigid shaft 108 is axially and longitudinally constrained in the distal hinge joint 112 by a bushing 113. The proximal drive shaft 106 is axially constrained in the proximal hinge joint 111 by bushing 114. The driver tip may be connected to the distal shaft 108 by means of a collet nut 115 or other appropriate coupler. The driver tip may be, for example, a screwdriver tip, a drill bit, a blade, a socket, an alien tip, a file, etc.

Referencing FIGS. 3 and 4, the articulating tool may be constructed and arranged to move between a first position and a second position. To change between the first and second positions the longitudinal position of the housing 110 may be altered with respect to the proximal drive shaft 106. As the longitudinal position of the housing 110 is altered with respect to the proximal drive shaft 106 the proximal drive shaft 106 moves longitudinally through bushing 114 thereby altering the free length of flexible drive shaft 107. As the free length of flexible drive shaft 107 decreases, the distal hinge joint moves away from the straight position to allow the flexible drive shaft to assume an arc of decreasing radius. Alternatively, as the free length of flexible drive shaft 107 increases, the distal hinge joint moves towards the straight position to allow the flexible drive shaft to assume an arc of increasing radius. Additionally, the drive shaft assembly, comprised of the proximal drive shaft 106, the flexible drive shaft 107, and the distal drive shaft 108, may be rotated simultaneously while the angle of articulation is adjusted. In another embodiment, the movement between a first and second position may be activated by other means such as, but not limited to, a cable drive system, a set of gears, a linkage or set of linkages, a pushrod or set of pushrods.

Referencing FIGS. 4 and 5, in another embodiment the articulating tool may include an antagonistic spring 116. The antagonistic spring 116 may be connected and extending through the proximal hinge joint 111 and the distal hinge joint 112. As the free length of flexible drive shaft 107 increases, the antagonist spring 116 may assist the distal hinge joint 112 in moving towards the aligned straight position.

Figure 6:
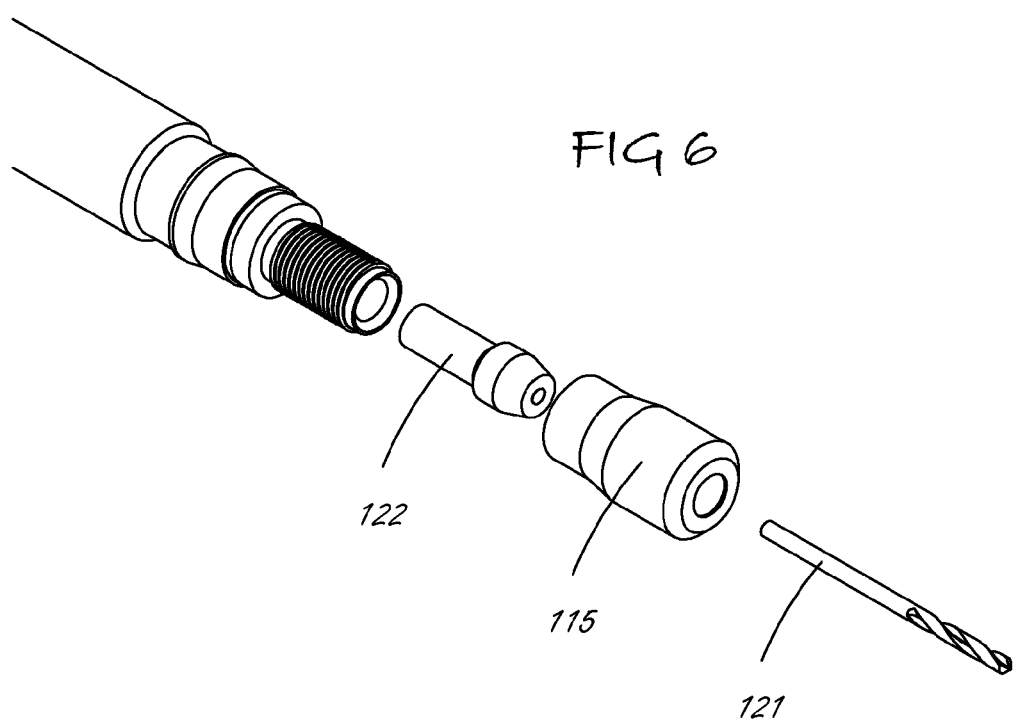
FIG. 6 illustrates an exploded view of an embodiment for attaching bits to the end of the articulating tool.

Referencing FIGS. 5 and 6, in another embodiment the articulating tool may include a slot or aperture in the proximal hinge joint 111 and the distal hinge joint 112. When the flexible drive shaft 107 assumes an arc of small radius at a high degree of articulation, the flexible drive shaft 107 may move or deflect a small distance from its neutral position or non-actuated position. The slot may allow for a portion of the flexible drive shaft 107 to deflect through the slot, thus allowing for full articulation.

Referencing FIGS. 3 and 4, the articulating tool may include a controller comprised of a controller housing 109, and controller handle 117. The proximal drive shaft 106 may be rigidly attached to a controller drive shaft 118 that is axially and longitudinally constrained to the controller housing 109 by bearings 119. The tool housing 110 may be constrained axially to the controller housing 109 by a sliding fit and longitudinally to the controller handle 109 by pins 120, a snap ring, etc. Threads on the controller housing 109 and the controller handle 117 may allow the longitudinal position between the controller housing 109 and the controller handle 117 to be adjusted by rotation of the controller handle 117 with respect to the controller housing 109. In this fashion, the relative longitudinal position of the proximal drive shaft 106 and the tool housing 110 may be adjusted due to their longitudinal constraint within the controller housing 109 and the controller handle 117, respectively. The controller housing 109 and the controller drive shaft 118 may be fashioned to attach to a surgical drill 101, manual driver handle, etc.

The controller may be capable of changing the articulating tool between a first and second position. In the first position, as shown in FIGS. 1 and 3, the distal hinge joint 112 and the distal drive shaft 108 are at a first angle, about 0°, with respect to the longitudinal axis of the housing 110. In the second position, as shown in FIGS. 2 and 4, the distal hinge joint 112 and the distal drive shaft 108 are at a second angle, θ, to with respect to the longitudinal axis of the housing 110. The angle θ may be anywhere from about 0° to about 60° and may allow full access a rib fracture site through a single thorax incision. Further, the articulating tool may be infinitely adjustable from about 0° to about 60° and may maintain that specific angle. In the first position, when the distal hinge joint 112 and the distal drive shaft 108 are at a first angle of about 0° with respect to the longitudinal axis of the housing 110, the articulating tool may be capable of fitting through a 12 mm trocar sleeve.

Figure 7:
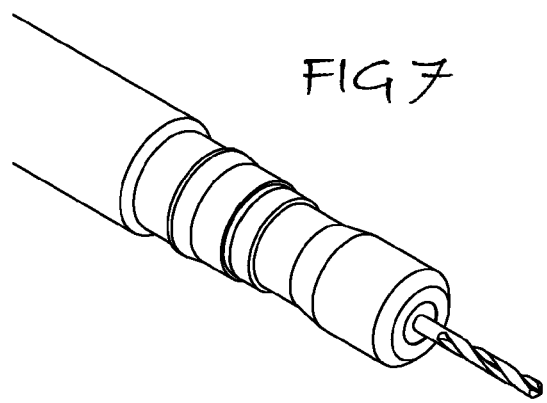
FIG. 7 illustrates a view of the same embodiment for attaching bits to the end of the articulating tool.

Referencing FIGS. 6 and 7, the distal drive shaft 108 may be fitted with a means of interchanging tips 121. The driver tip may be, for example, a screwdriver tip, a drill bit, a blade, a socket, an alien tip, a file, etc. In one embodiment, the articulating tool incorporates a collet 122 and collet nut 115 to allow attaching, detaching, interchanging, or replacing of a tip.

Figure 8:
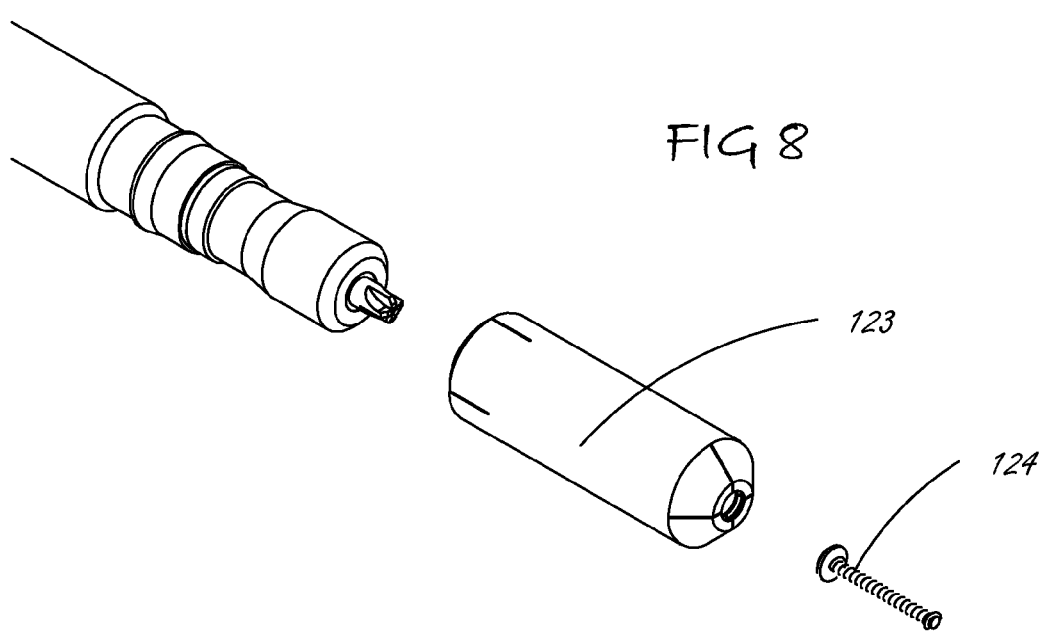
FIG. 8 illustrates an exploded view of a first embodiment of a fastener retainer at the end of the articulating tool.
Figure 9:
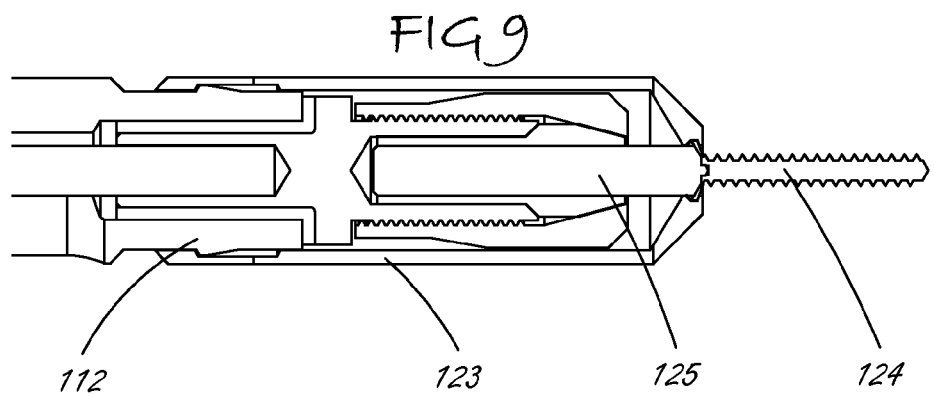
FIG. 9 illustrates a cross-sectional view from one side of the first embodiment of a fastener retainer at the end of the articulating tool, wherein the fastener is in a fixed position.
Figure 10:
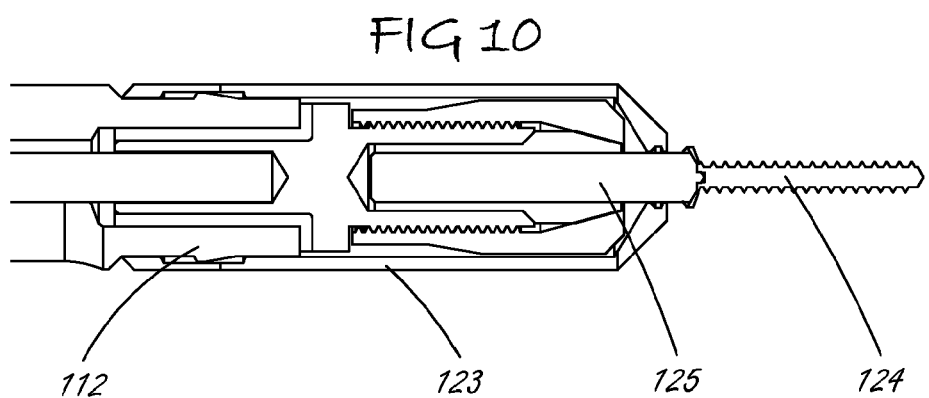
FIG. 10 illustrates a cross-sectional view from one side of the first embodiment of a fastener retainer at the end of the articulating tool, wherein the fastener is in a free position.

Referencing FIGS. 8-10, in another embodiment the articulating tool may accept a fastener retainer 123. The fastener retainer 123 may hold a fastener 124 onto a driver tip 125 by attaching to the distal hinge joint 112. The fastener retainer 123 may include a grooved feature at the distal end to accept the fastener head 124, where the rim of the groove has an inner diameter smaller than the largest diameter of the fastener head 124. The fastener retainer 123 may be designed with slots to decrease the stiffness of the grooved feature and allow the fastener 124 to be dislodged by elastic deformation of the fastener retainer. The fastener retainer 123 may have a proximal groove to allow the fastener retainer to clip onto a ridge feature on the distal hinge joint 112, as shown in FIG. 9. The proximal groove in retainer 123 may be wide enough to allow the fastener retainer to slide longitudinally along the distal hinge joint between a first position shown in FIG. 9 and a second position shown in FIG. 10. The first position may hold the fastener head 124 firmly on the driver bit 125 such that the fastener 124 can be safely delivered to point of installation. The second position is proximal relative to the first position and may release the fastener head 124 from the distal groove feature. As the fastener 124 fully seats in bone or other material, the fastener retainer 125 is forced from the first to the second position, thereby releasing the fastener 124 without external actuation.

Figure 11:
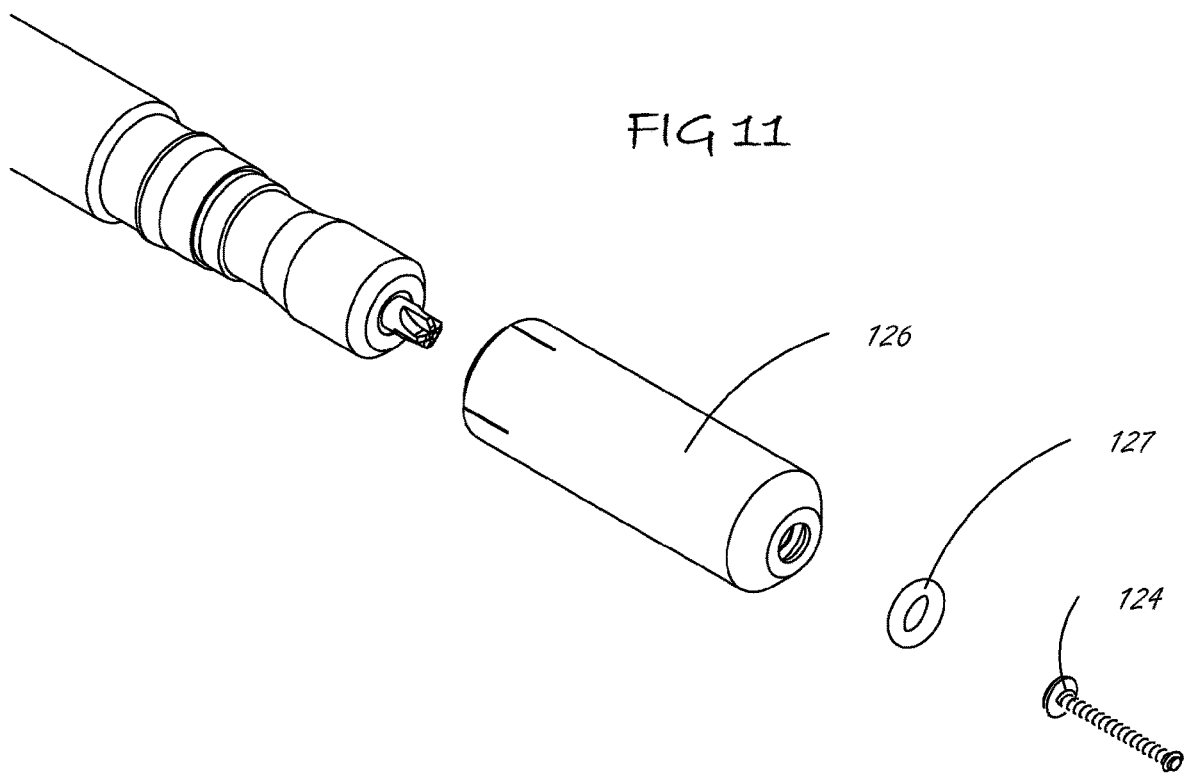
FIG. 11 illustrates an exploded view of a second embodiment of a fastener retainer at the end of the articulating tool.
Figure 12:
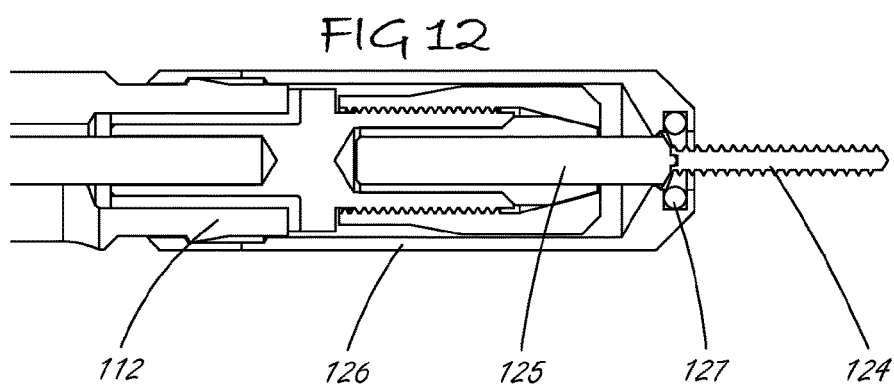
FIG. 12 illustrates a cross-sectional view from one side of the second embodiment of a fastener retainer at the end of the articulating tool, wherein the fastener is in a fixed position.
Figure 13:
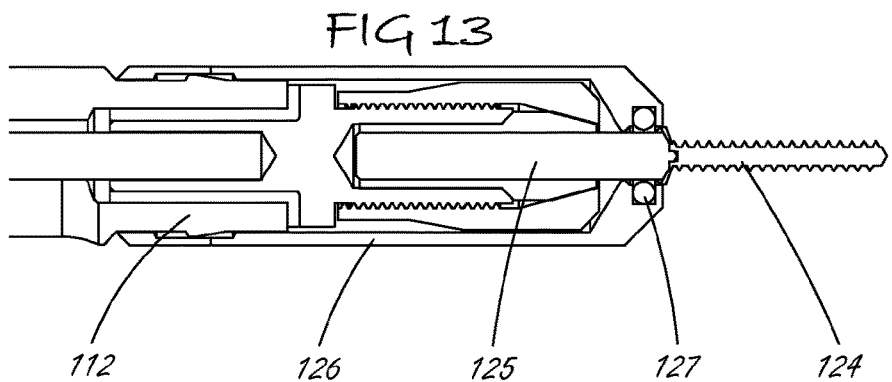
FIG. 13 illustrates a cross-sectional view from one side of the second embodiment of a fastener retainer at the end of the articulating tool, wherein the fastener is in a free position.

Referencing FIGS. 11-13, in another embodiment the articulating tool may accept a fastener retainer 126. The fastener retainer 126 may hold a fastener 124 onto a driver tip 125 by attaching to the distal hinge joint 112. The fastener retainer 126 may include a groove to receive a soft compliant element 127, at the distal end to accept the fastener head 124, where the inner diameter of the compliant element 127 is smaller than the largest diameter of the fastener head 124. This arrangement allows the fastener 124 to be dislodged from the elastic element 127 by applying a reasonable level of longitudinal force. The fastener retainer 126 may have a proximal groove to allow the fastener retainer to clip onto a ridge feature on the distal hinge joint 112, as shown in FIG. 9. The proximal groove in retainer 126 may be wide enough to allow the fastener retainer to slide longitudinally along the distal hinge joint between a first position shown in FIG. 12 and a second position shown in FIG. 13. The first position may hold the fastener head 124 firmly on the driver bit 125 such that the fastener 124 can be safely delivered to point of installation. The second position is proximal relative to the first position and may release the fastener head 124 from the distal groove feature. As the fastener 124 fully seats in bone or other material, the fastener retainer 126 and compliant element 127 are forced from the first to the second position, thereby releasing the fastener 124 without external actuation.

In another aspect a method of using an embodiment of the articulating tool for thoracoscopic surgery is described. In one embodiment of the method the articulating tool may be used for minimally invasive internal fixation of rib fractures using video-assisted thoracic surgery (VATS) to place fasteners in osteosynthetic implants. VATS is a well-established procedure for pulmonary resection, lung volume reduction, lung biopsy, and pericardial resection. By selectively ventilating one lung with a dual lumen endotracheal tube, much of the pleural cavity may become accessible. An embodiment of the articulating tool may be an appropriate device for fastener delivery using VATS fixation of rib fractures. Further, the embodiments of the articulating tool described herein may be articulated within the thoracic cavity to allow placement of fasteners normal to the local surface of a curved rib.

Referencing FIG. 14, an embodiment of a method of using the articulating tool to perform minimally invasive internal fixation of rib fractures is illustrated. While FIG. 14 illustrates a number of steps, any step or steps may be added or removed, and the steps may be performed in any order. The method described is the preferred embodiment, however the method may be performed in alternative body cavities, may be performed with any operable tip known to the art, or may be performed to secure any device known to the art to body tissue.

The method of minimally invasive rib fixation using an embodiment of the articulating tool may include intubating the patient with a dual lumen endotracheal tube and selectively deflating one lung 128. The method may include making a series of small incision in the thorax 129 such that trocar sleeves can be placed 130, allowing the insertion of a camera 131. Under the guidance of the camera, an osteosynthetic implant may be inserted and contoured to the rib 132 using tools known to the art. An embodiment of the articulating tool with a drill bit attached as the operable bit may be inserted through a trocar sleeve 133. Under the guidance of the camera, the embodiment of the articulating tool may be adjusted to the appropriate angle for accessing a particular operating site 134.

The method may include adjusting the placement of the osteosynthetic implant for use as a drilling template 135 using tools known to the art and drilling pilot holes 135 by applying torque to the articulating tool. After performing a task, the articulating tool may be straightened by manipulating its controller 136 and withdrawn from the thoracic cavity 137.

The method may further include utilizing a driver bit as the operable tip with a fastener 138. The fastener may be held in place with a fastener retainer 138. The articulating tool may be inserted through a trocar sleeve 139. Under the guidance of the camera, the embodiment of the articulating tool may be adjusted to the appropriate angle for accessing a particular operating site 140. Torque may be applied to the articulating tool to drive the fastener into the rib 141, at which time the fastener retainer may release the fastener. The fastener may secure an osteosynthetic implant to the rib. After performing a task, the articulating tool may be straightened by manipulating its controller 142 and withdrawn from the thoracic cavity 143. Steps 138 through 143 may be repeated several times to deliver multiple fasteners.

While the invention has been described and illustrated in connection with preferred embodiments for use in surgery, many variations and modifications will be evident to those skilled in the art and may be made without departing from the spirit and scope of the invention. The invention is thus not to be limited to the precise details of methodology or construction set forth above as such variations and modification are intended to be included within the scope of the invention.

We claim:

1. An articulating tool, comprising:
   a housing having a proximal housing end and a distal housing end, the proximal housing end being pivotably connected to the distal housing end by an articulating joint;
   a rotatable drive shaft within the housing having at least a proximal shaft portion, a medial shaft portion, and a distal shaft portion, wherein at least the medial shaft portion is non-rigid, and wherein the proximal shaft portion extends through the proximal housing end and the medial shaft portion extends through the articulating joint;
   an operable tip connected to the distal shaft portion, the articulating tool being constructed and arranged to have at least a first configuration and a second configuration, in the first configuration the operable tip being at a first angle with respect to the longitudinal axis of the housing, and in the second configuration a relative longitudinal position of the rotatable drive shaft being altered with respect to the proximal housing end and the operable tip being at a second angle with respect to the longitudinal axis of the housing;
   a controller connected to the proximal housing end and comprising a controller housing and a controller handle with complementary threads, wherein rotating the controller handle with respect to the controller housing changes the tool between the first configuration and the second configuration by altering the relative longitudinal position of the rotatable drive shaft with respect to the proximal housing end; and
   a drive mechanism configured to apply torque to the rotatable drive shaft;
   wherein the medial shaft portion is elastically flexible.

2. The articulating tool of claim 1, wherein the operable tip includes a driver bit and a retainer for a fastener having a head, wherein the retainer includes a compliant element having an inner diameter smaller than an outer diameter of the head of the fastener, wherein the retainer is configured to be movable between a first position and a second position with respect to the fastener, and wherein the fastener is released from the retainer in the second position.

3. The articulating tool of claim 1, wherein the operable tip includes a drill bit.

4. The articulating tool of claim 1, wherein the operable tip includes a driver bit and a retainer for a fastener.

5. An articulating tool, comprising:
   a housing having a proximal housing end and a distal housing end, the proximal housing end being pivotably connected to the distal housing end by an articulating joint;
   a rotatable drive shaft within the housing having at least a proximal shaft portion, a medial shaft portion, and a distal shaft portion, wherein at least the medial shaft portion is non-rigid, and wherein the proximal shaft portion extends through the proximal housing end and the medial shaft portion spans the articulating joint;
   an operable tip connected to the distal shaft portion;
   a controller connected to the proximal housing end and comprising a controller housing and a controller handle with complementary threads, wherein rotating the controller handle with respect to the controller housing alters a distance between a proximal end of the rotatable drive shaft and the articulating joint to change an angle of the operable tip with respect to a longitudinal axis of the housing; and
   a drive mechanism configured to apply torque to the rotatable drive shaft.

6. The articulating tool of claim 5, wherein the medial shaft portion is elastically flexible.

7. The articulating tool of claim 5, wherein the operable tip includes a drill bit.

8. The articulating tool of claim 5, wherein the operable tip includes a driver bit and a retainer for a fastener.

9. The articulating tool of claim 8, wherein the retainer includes a compliant element having an inner diameter smaller than an outer diameter of a head of the fastener, wherein the retainer is configured to be movable between a first position and a second position with respect to the fastener, and wherein the fastener is released from the retainer in the second position.

10. The articulating tool of claim 5, further comprising an antagonistic spring connected to the articulating joint.

11. An articulating tool, comprising:
a housing having a proximal housing end and a distal housing end, the proximal housing end being pivotably connected to the distal housing end by an articulating joint;
a rotatable drive shaft within the housing having at least a proximal shaft portion, a medial shaft portion, and a distal shaft portion, wherein at least the medial shaft portion is non-rigid, and wherein the proximal shaft portion extends through the proximal housing end and the medial shaft portion spans the articulating joint;
an operable tip connected to the distal shaft portion;
a controller connected to the proximal housing end and comprising a controller housing and a controller handle with complementary threads, wherein rotating the controller handle with respect to the controller housing alters a relative longitudinal position of the rotatable drive shaft with respect to the proximal housing end to adjust a tension on the rotatable drive shaft, such that the rotatable drive shaft actuates the operable tip to change an angle of the operable tip with respect to a longitudinal axis of the housing; and
a drive mechanism configured to apply torque to the rotatable drive shaft.

* * * * *